United States Patent
Kelleher et al.

(10) Patent No.: US 10,342,690 B2
(45) Date of Patent: Jul. 9, 2019

(54) DEVICE AND METHOD FOR ENDOLUMINAL THERAPY

(71) Applicant: Brian Kelleher, San Diego, CA (US)

(72) Inventors: Brian Kelleher, Del Mar, CA (US); Corbett Stone, Poway, CA (US)

( * ) Notice: Subject to any disclaimer, the term of this patent is extended or adjusted under 35 U.S.C. 154(b) by 48 days.

(21) Appl. No.: 15/269,983

(22) Filed: Sep. 20, 2016

(65) Prior Publication Data

US 2017/0014253 A1    Jan. 19, 2017

Related U.S. Application Data

(60) Continuation of application No. 13/903,704, filed on May 28, 2013, which is a continuation of application No. 12/710,038, filed on Feb. 22, 2010, now Pat. No. 8,449,558, which is a division of application No. 10/659,211, filed on Sep. 9, 2003, now Pat. No. 7,666,195.

(60) Provisional application No. 60/409,838, filed on Sep. 9, 2002.

(51) Int. Cl.
*A61F 5/00*  (2006.01)
*A61B 17/06*  (2006.01)
*A61B 17/04*  (2006.01)
*A61B 17/00*  (2006.01)
*A61B 17/062*  (2006.01)

(52) U.S. Cl.
CPC ........ *A61F 5/0083* (2013.01); *A61B 17/0469* (2013.01); *A61B 17/0482* (2013.01); *A61B 17/0485* (2013.01); *A61B 17/0491* (2013.01); *A61B 17/06066* (2013.01); *A61B 17/0625* (2013.01); *A61B 2017/00026* (2013.01); *A61B 2017/00296* (2013.01); *A61B 2017/00349* (2013.01); *A61B 2017/00566* (2013.01); *A61B 2017/00827* (2013.01); *A61B 2017/047* (2013.01); *A61B 2017/0417* (2013.01); *A61B 2017/0472* (2013.01); *A61B 2017/06052* (2013.01); *A61B 2505/05* (2013.01)

(58) Field of Classification Search
CPC ............. A61F 5/0083; A61B 2017/047; A61B 2017/0472; A61B 17/0469; A61B 17/0482; A61B 17/0485; A61B 17/0491; A61B 17/06066
See application file for complete search history.

(56) References Cited

U.S. PATENT DOCUMENTS

| | | |
|---|---|---|
| 5,356,424 A | 10/1994 | Buzerak et al. |
| 5,984,932 A | 11/1999 | Yoon |
| 6,071,292 A | 6/2000 | Makower et al. |

(Continued)

*Primary Examiner* — Tuan V Nguyen
(74) *Attorney, Agent, or Firm* — Merle W Richman, III

(57) ABSTRACT

A device and method for selectively engaging or penetrating a layer of a luminal organ wall where the luminal organ wall has a plurality of layers including an outermost layer and an innermost layer adjacent to the lumen of the organ. The device and method select one of the plurality of layers of the organ wall other than the innermost layer and deploy from within the lumen of the organ a tissue device through the innermost layer to a specific depth to engage or penetrate the selected one of the plurality of layers. The device and method may be employed to create luminal pouches or restrictive outlets. In a stomach organ, the device and methods may be employed to treat obesity by forming a gastric pouch with or without a restrictive outlet.

9 Claims, 44 Drawing Sheets

(56) References Cited

U.S. PATENT DOCUMENTS

| | | |
|---|---|---|
| 6,193,733 B1 | 2/2001 | Adams |
| 6,478,791 B1 | 11/2002 | Carter et al. |
| 6,558,400 B2 | 5/2003 | Deem et al. |
| 6,663,639 B1 | 12/2003 | Laufer et al. |
| 6,706,044 B2 | 3/2004 | Kuslich et al. |
| 7,063,715 B2 | 6/2006 | Onuki et al. |
| 7,297,150 B2 | 11/2007 | Cartledge et al. |
| 7,666,195 B2 | 2/2010 | Kelleher et al. |
| 8,449,558 B2 | 5/2013 | Kelleher et al. |
| 2002/0082621 A1* | 6/2002 | Schurr ............... A61B 17/0643 606/151 |
| 2002/0183768 A1* | 12/2002 | Deem .................. A61B 17/064 606/151 |
| 2003/0040804 A1 | 2/2003 | Stack et al. |
| 2003/0109892 A1 | 6/2003 | Deem et al. |
| 2003/0199989 A1 | 10/2003 | Stack et al. |
| 2004/0006351 A1 | 1/2004 | Gannoe et al. |
| 2004/0009224 A1 | 1/2004 | Miller |
| 2004/0024386 A1 | 2/2004 | Deem et al. |
| 2004/0092892 A1 | 5/2004 | Kagan et al. |
| 2004/0117031 A1 | 6/2004 | Stack et al. |
| 2004/0210243 A1 | 10/2004 | Gannoe et al. |

\* cited by examiner

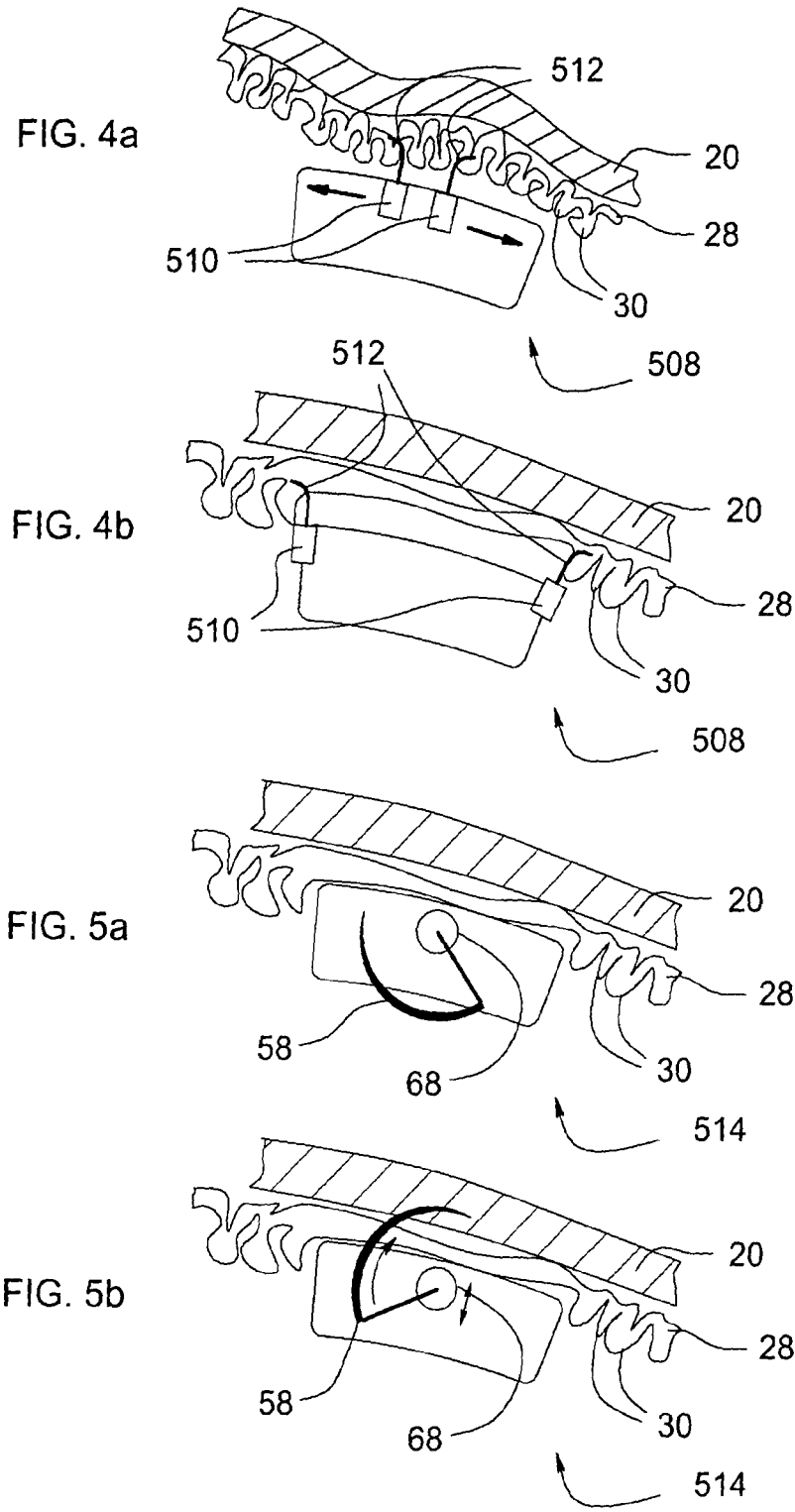

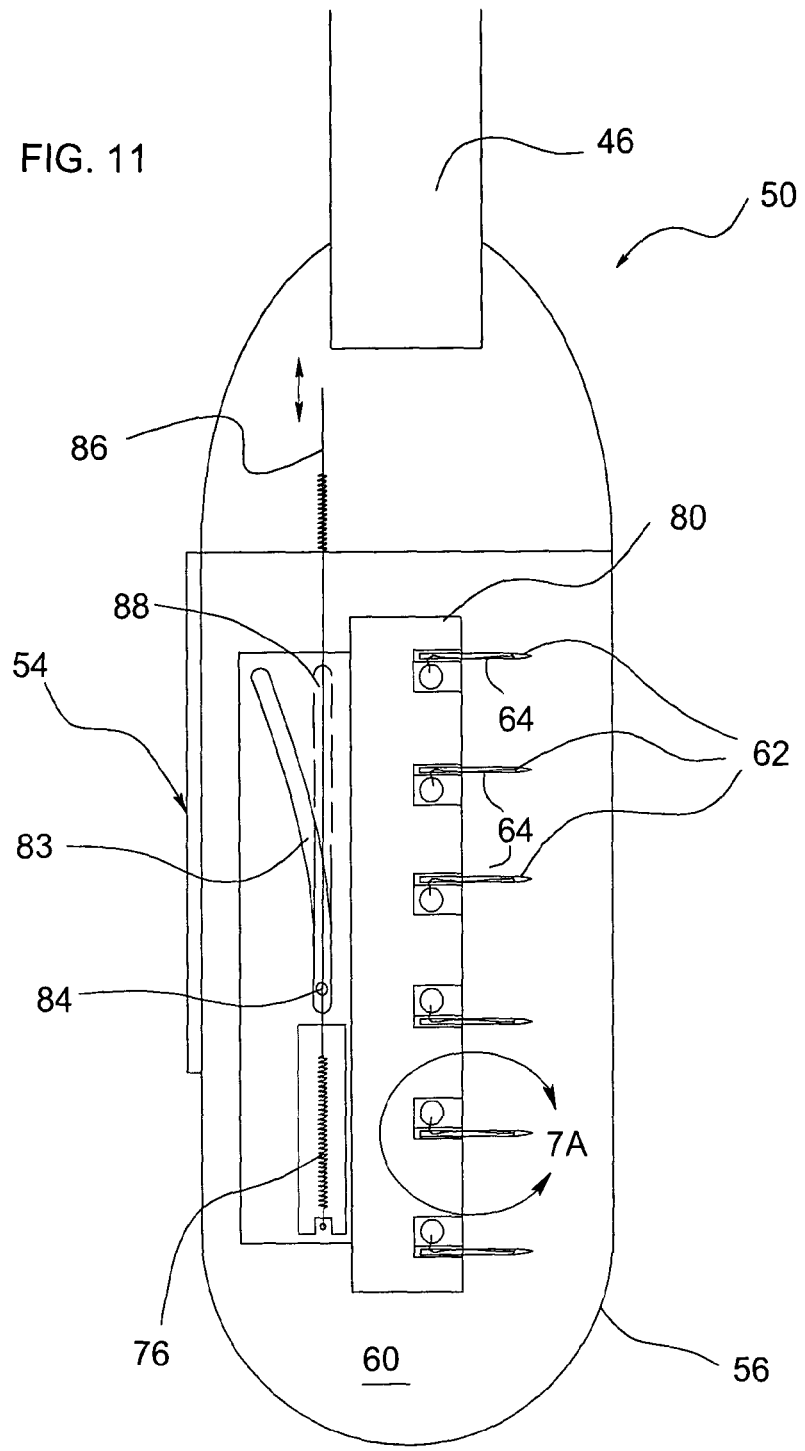

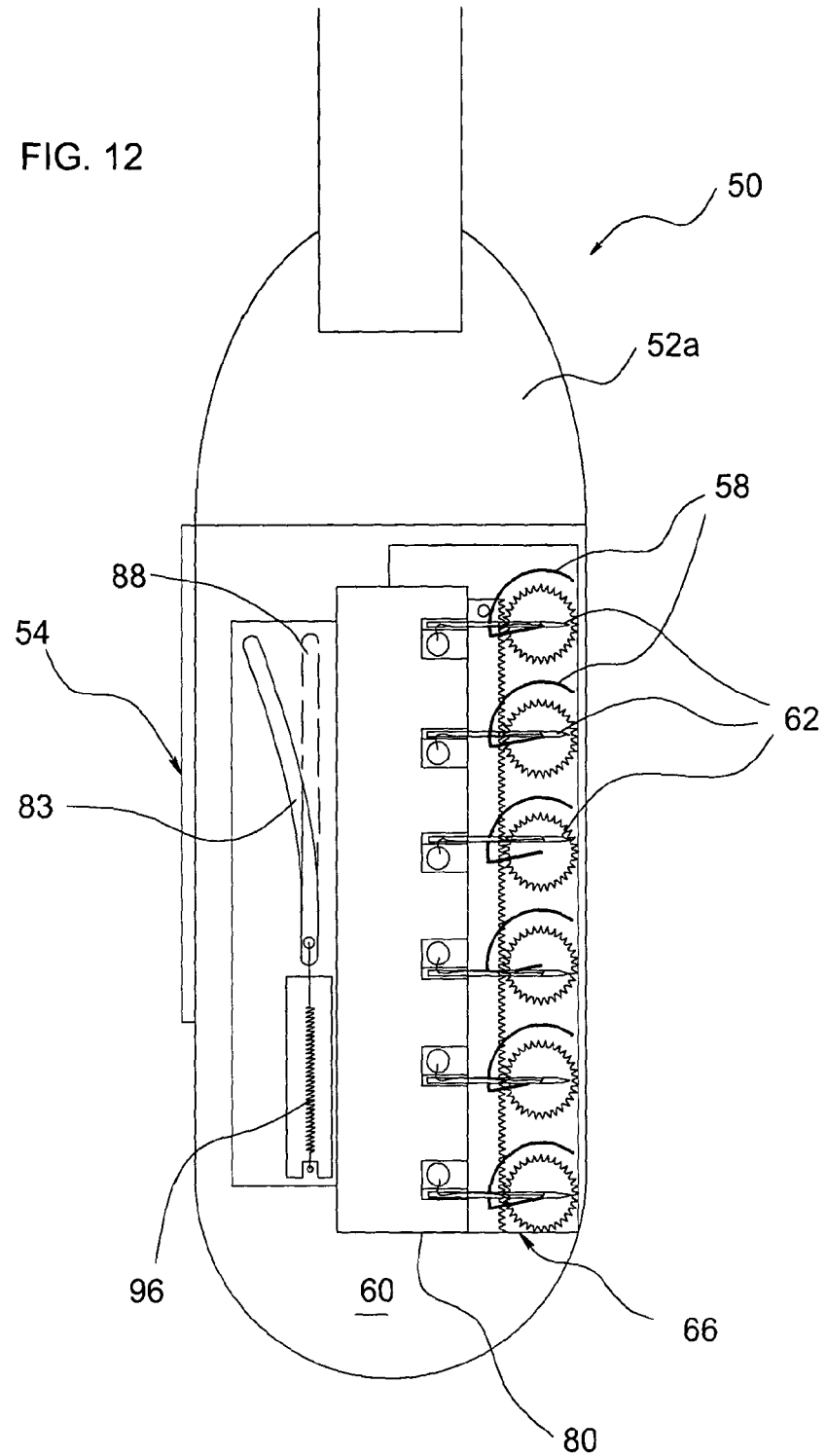

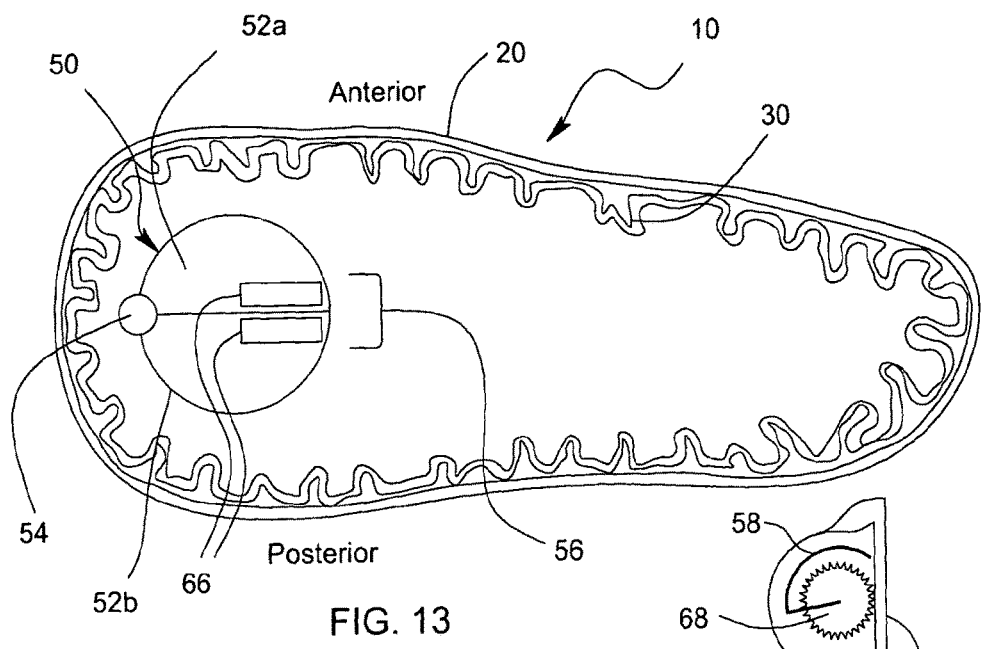
FIG. 13
FIG. 13a
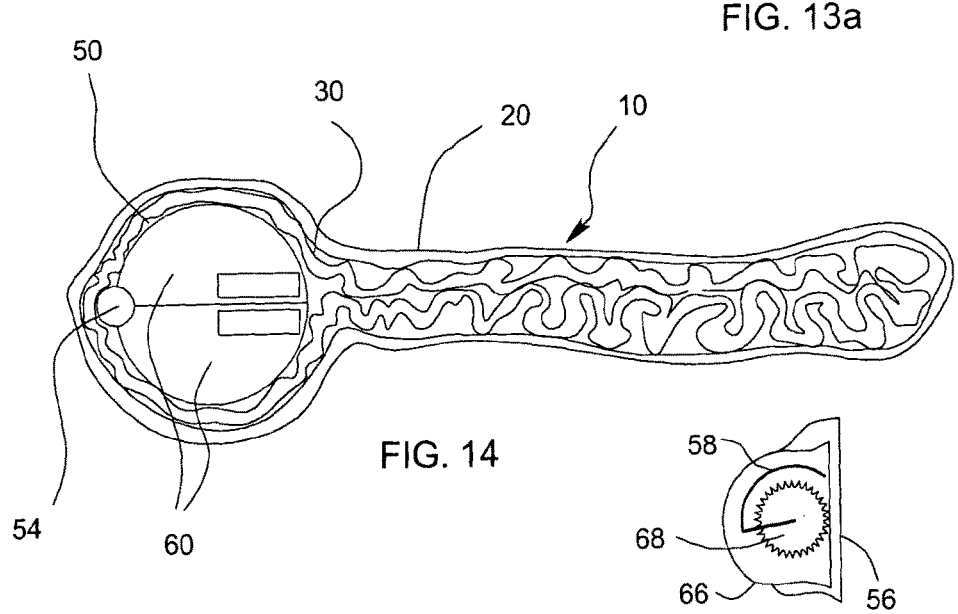
FIG. 14
FIG. 14a

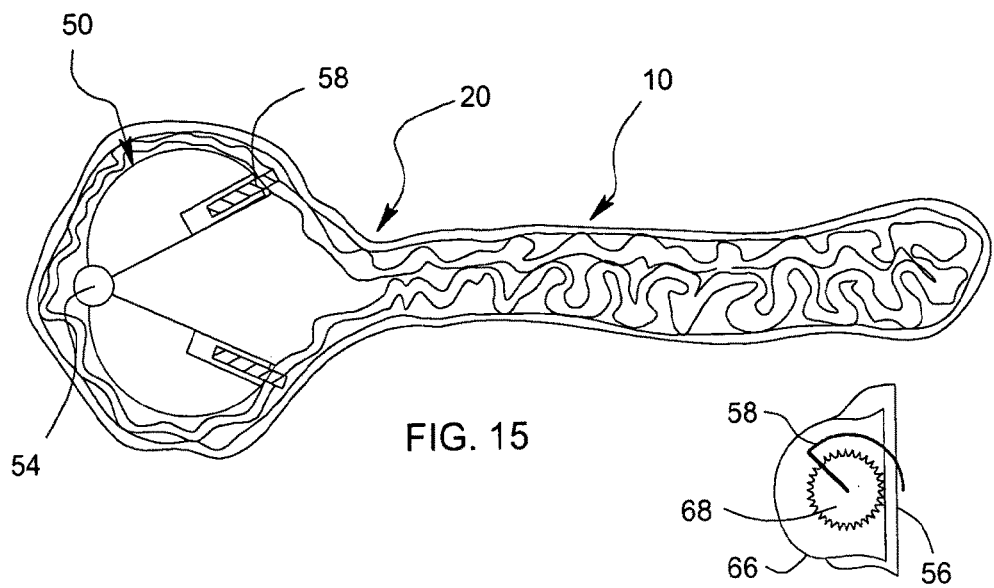
FIG. 15
FIG. 15a
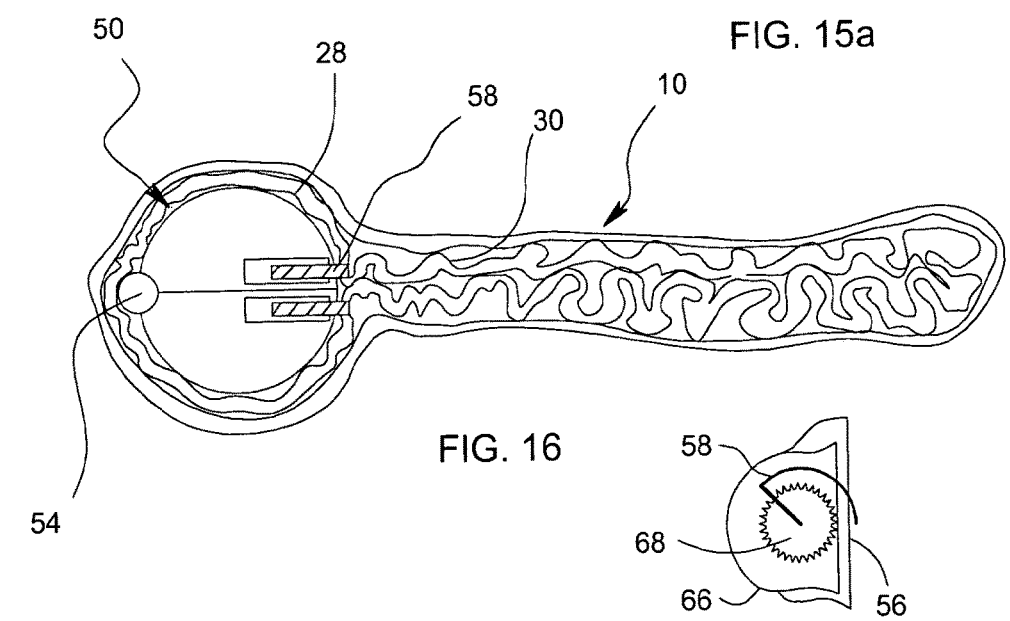
FIG. 16
FIG. 16a

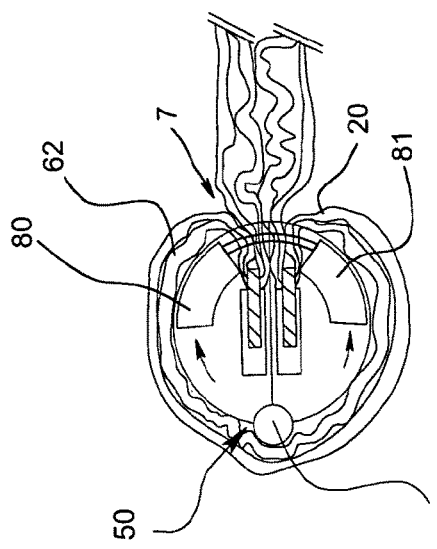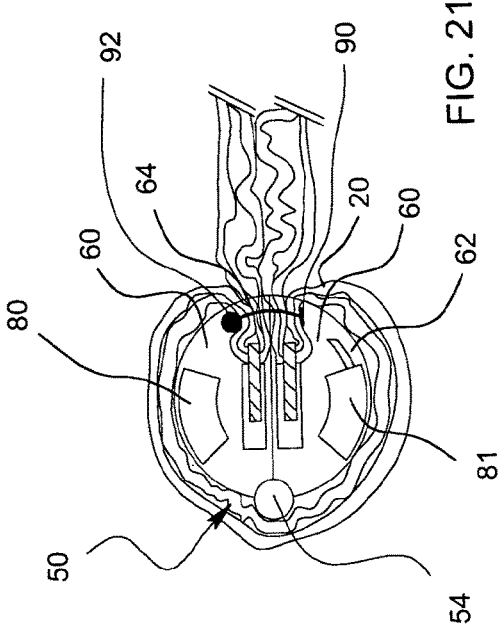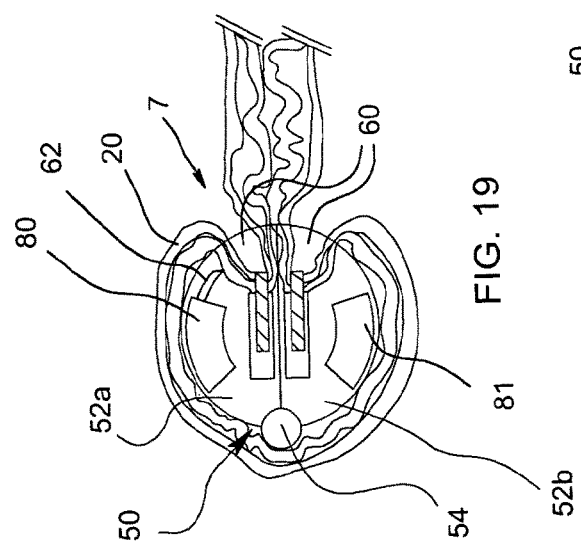

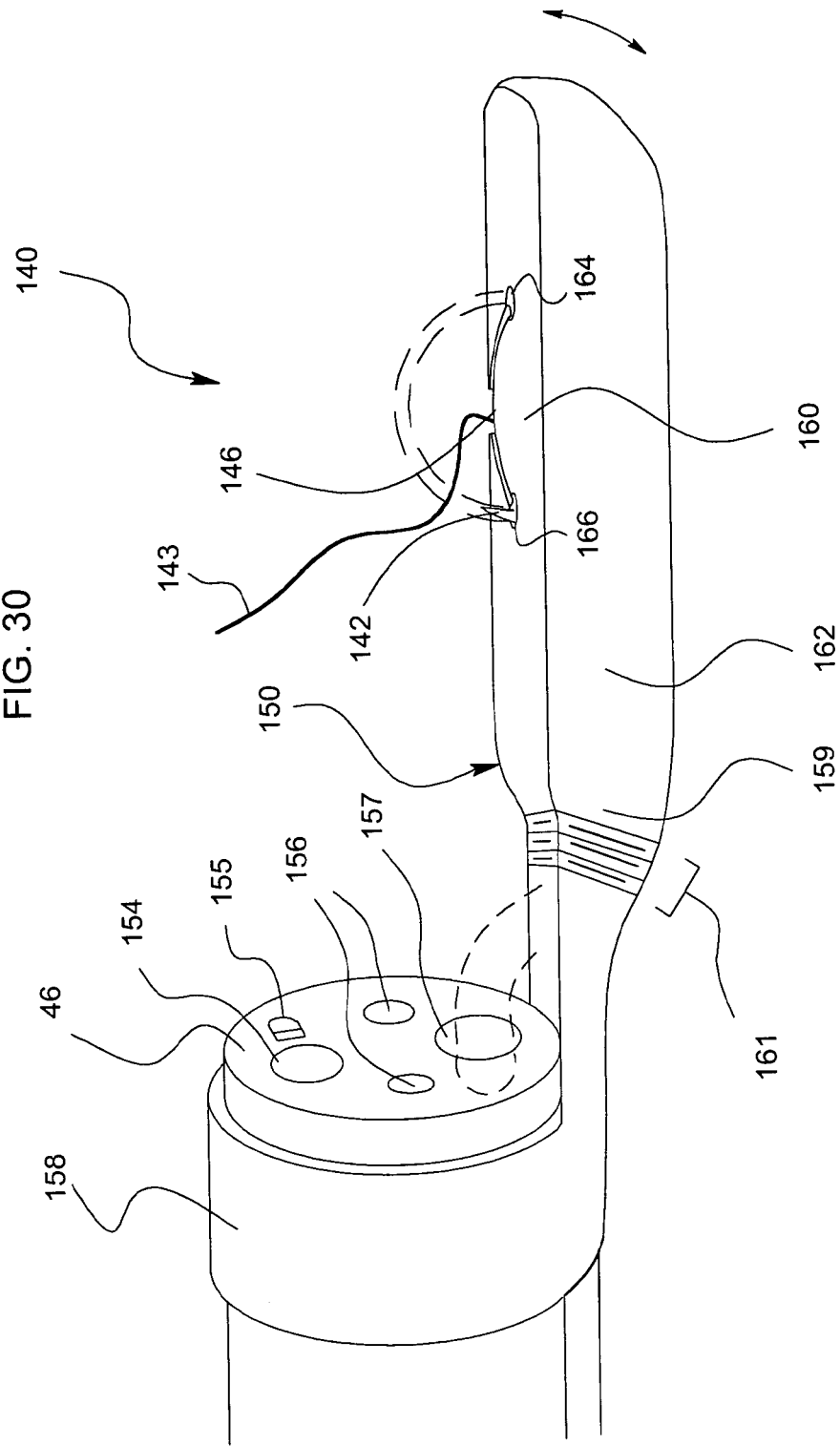

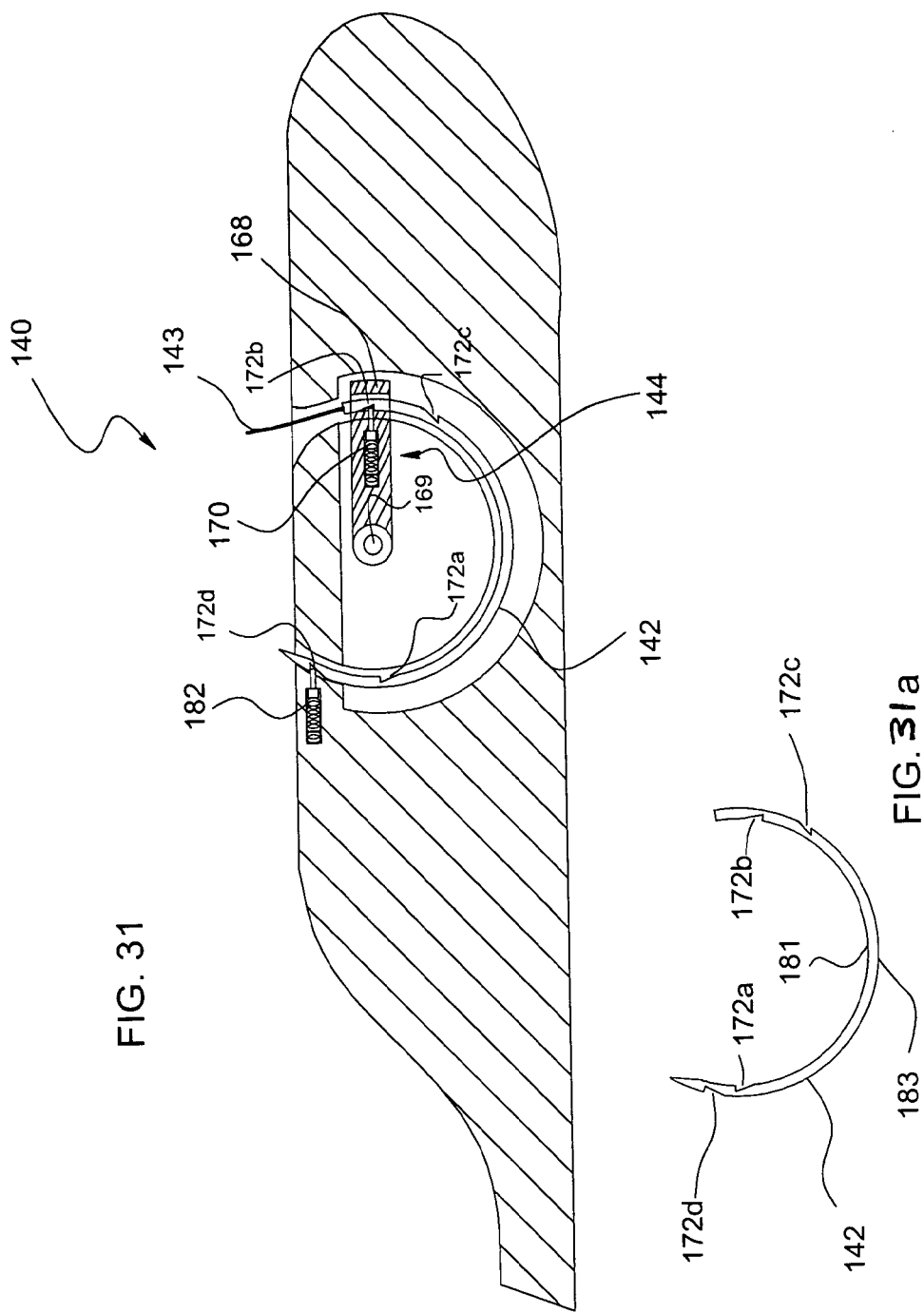

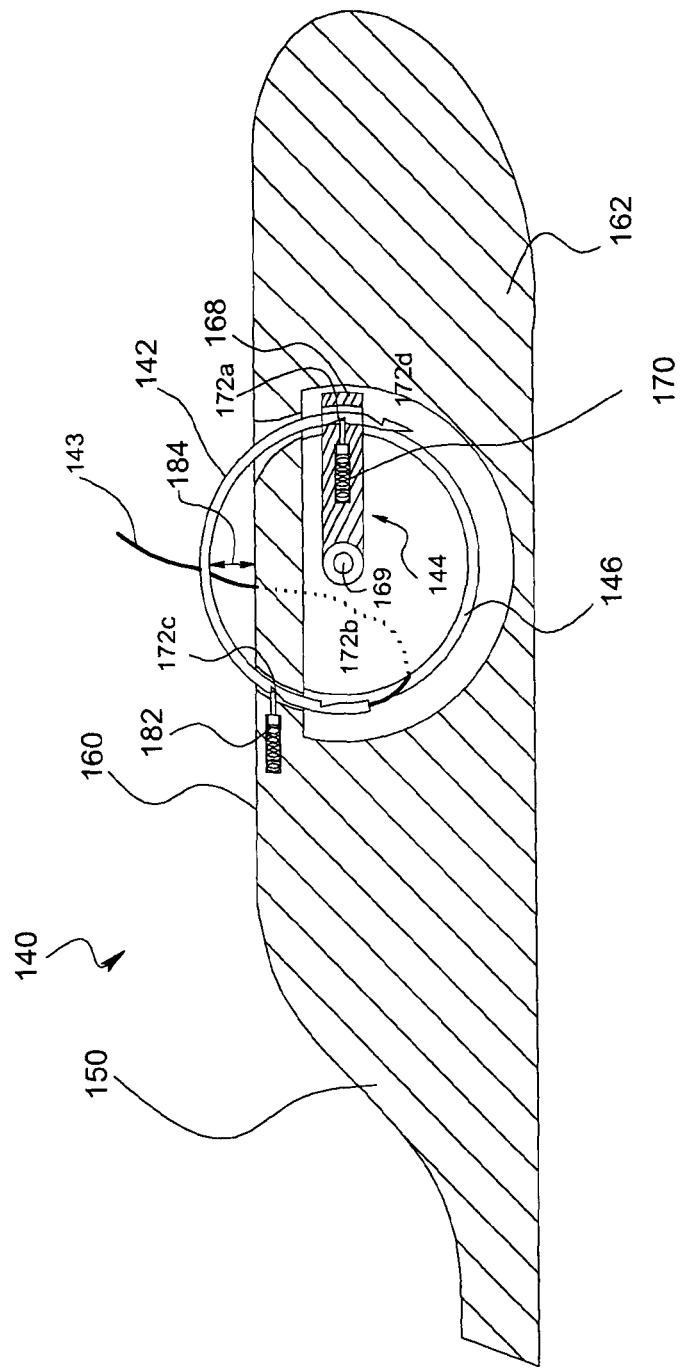

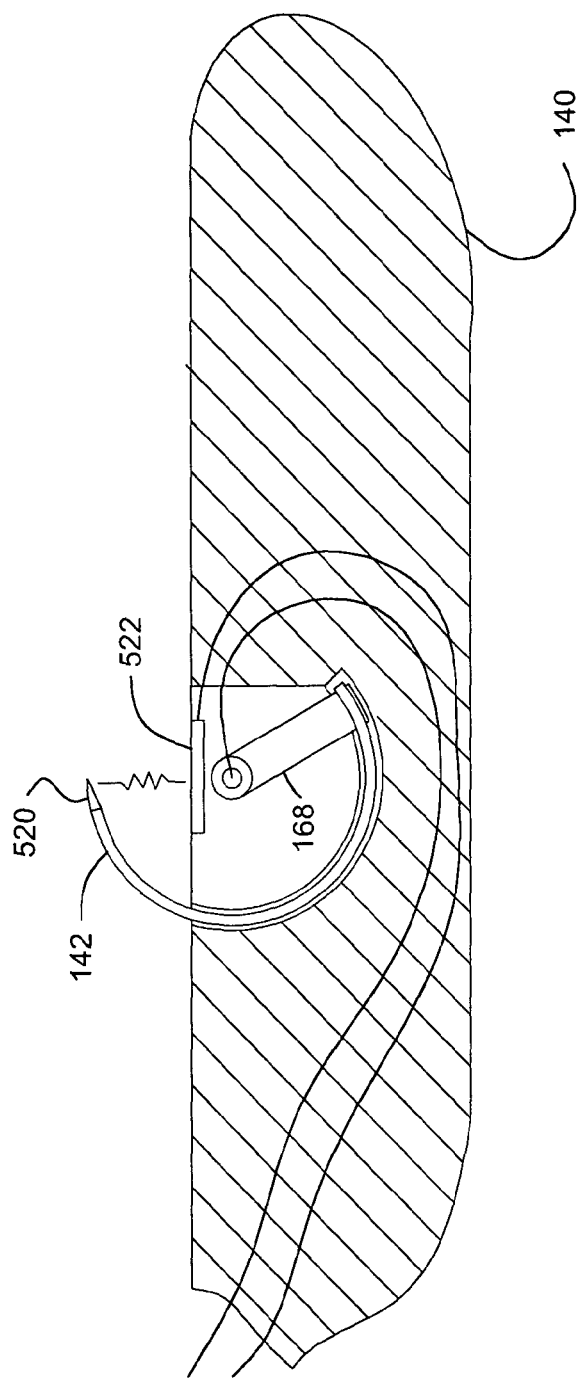

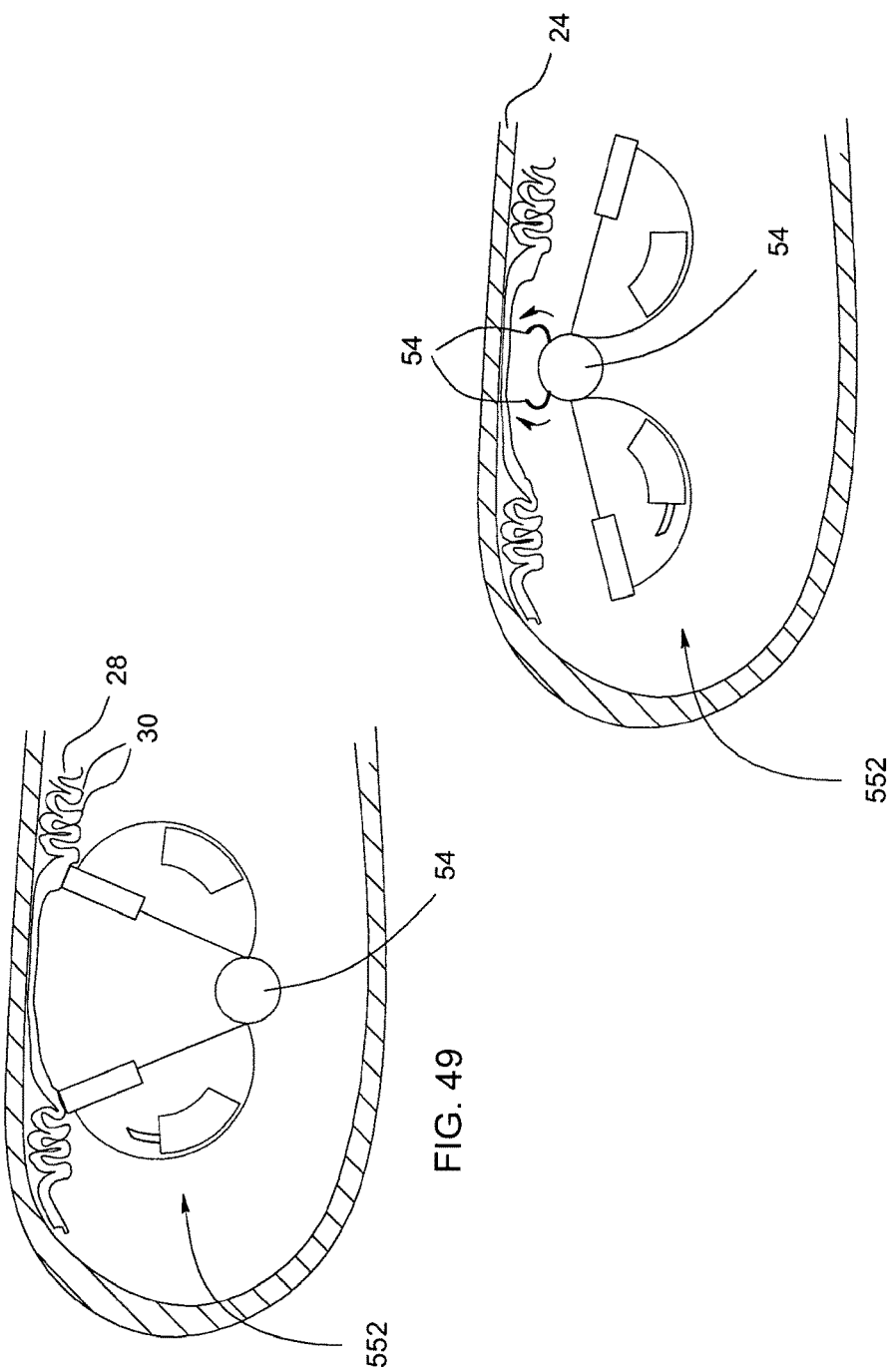

DEVICE AND METHOD FOR ENDOLUMINAL THERAPY

CROSS REFERENCE TO RELATED APPLICATIONS

The present application is a continuation application and claims the benefit of priority of U.S. application Ser. No. 13/903,704, entitled "Device and Method for Endoluminal Therapy", filed on May 28, 2013, which is a continuation application and claims the benefit of priority of U.S. application Ser. No. 12/710,038, entitled "Device and Method for Endoluminal Therapy", filed on Feb. 22, 2010, Attorney Docket END001US1, issued as U.S. Pat. No. 8,449,558, which is a divisional application thereof and claims the benefit of priority of U.S. application Ser. No. 10/659,211, entitled "Device and Method for Endoluminal Therapy", filed on Sep. 9, 2003, issued as U.S. Pat. No. 7,666,195 and claims the benefit of priority of Provisional Patent Application 60/409,838, entitled "Method and Apparatus for Treating Obesity", filed on Sep. 9, 2002, the entirety of each is incorporated by reference.

BACKGROUND

Field of the Invention

The invention relates to endoluminal therapy, and, in particular, to methods and devices for securement of hollow organs, including gastric restriction procedures in the stomach for treating obesity and gastroesophageal reflux disease (GERD).

Description of the Related Art

Flexible endoscopic therapy of the hollow organs such as the stomach, intestines and esophagus has been shown to have fewer complications and faster recovery times than traditional or laparoscopic surgery. As such, there is a growing interest in expanding the capabilities of such therapy. In particular, there is a desire to perform organ modification, for example gastroplasty, from within the lumen of the organ through a trans-luminal route using flexible endoscopic tools.

Until now, there have been no practical devices available to enable procedures such as endoluminal plasty in a safe and reliable manner. The most challenging part of such a procedure is the placement of durable securement elements, such as sutures, through the full thickness of the organ walls in order to secure portions of the organ together or to attach elements to the wall. The reason securement element placement is challenging is that the organ wall may consist of multiple layers, each having unique physical properties. For example, the stomach has three primary wall layers including an innermost layer is the mucosa, the middle layer is the muscularis, and the outermost layer is the serosa. The mucosa is a relatively fragile layer and is loosely connected to the muscularis. The mucosa typically comprises a plurality of folds, called rugal folds, or rugae, which make the thickness of the mucosal layer highly variable and unpredictable. Securement elements anchored in the mucosa have been shown to pull out over time. The muscularis is somewhat tougher; although securement elements placed there may still pull out over time if they are placed under tension, as is the case for gastroplasty. In the stomach, the serosa layer is thin but is the toughest of the three layers. It is believed that to create durable securement of the stomach wall, securement elements need to pass through the serosa. This presents a challenge for endoluminal therapy, however, since the combined thickness of the three layers of the stomach wall is normally unpredictable.

In order to deploy a securement element that consistently passes through an ideal layer of an organ wall, the length of the securement element or the depth of deployment needs to accurately engage the desired layer. When the desired layer of a wall is the outermost layer, surrounding structures may be in danger of being engaged by such securement element or deployment device.

There is therefore a need for devices and methods to safely and reliably deploy securement mechanisms to a desired layer of the organ wall without endangering surrounding structures.

Another challenge of endoluminal devices intended for use in organ therapy is the engagement and movement of regions of the organ wall in order to approximate and secure multiple locations. Existing endoscopic tools for grabbing, such as grasping forceps, tend to engage only the innermost layer, the mucosa in an exemplary organ, the stomach. It may require a significant amount of force to move a region of the organ wall, pulling by the innermost layer may tear it. A more reliable method of moving the wall is to engage other layers. Further, the process of approximating two regions of the wall may require multiple instruments.

There is, therefore, a need for methods and devices to approximate multiple regions of the wall within a hollow organ, and specifically to selectively engage the muscularis within the stomach wall. There is a further need for instruments that combine the above steps of engaging, approximating and securing multiple regions of the wall of a hollow organ, such instruments being further refined to enable a specific endoluminal procedure such as gastroplasty.

In an organ, it may be desirable to modify the flow rate or pressure of materials or fluids that propagate through the organ's lumen.

There is thus a need for methods and devices to create a restrictive outlet to a luminal pouch from within the lumen of the organ.

Organ wall approximation and restrictive outlet performance may diminish over time as the organ wall dilates due to luminal pressure.

There is, therefore, a need for methods and devices to reduce the amount of permanent dilation that an organ wall undergoes following modification procedures.

SUMMARY

The preferred methods and devices described herein provide for advanced endoluminal procedures involving hollow organs. Such advanced procedures involve selective engagement of a target layer within the wall of a hollow organ, approximation of multiple regions of the wall, and safe and reliable placement of securement elements through the full thickness of the wall without endangering structures surrounding the hollow organ. Specific methods and devices described enable endoluminal procedures such as gastroplasty for the treatment of obesity and GERD, involving the formation of a gastric pouch or partition and a restrictive outlet. Further methods and devices provide for minimizing the dilation of the pouch or restrictive outlet over time.

In one of more preferred embodiments of the invention, devices and methods are described for selectively engaging a target layer within the wall of a hollow organ. In one exemplary embodiments, the innermost wall layer of an organ is manipulated to flatten out the folds and thereby make the depth required to reach an inner layer more predictable. The flattening may be done by insufflation, or by stretching or pressing out the folds. Either during or after the flattening of the innermost wall layer, a tissue engagement mechanism or tissue penetration element may be brought into close contact with the innermost wall layer and the tissue mechanism or element may be deployed to a specific depth, which may be adjustable. In one or more additional embodiments, an electrical impedance measurement system may be employed to measure the impedance of an organ wall at various depths, in order to provide data on the thickness of various layers prior to deployment of the mechanism or element, or to provide feedback regarding actual progress of the mechanism or element as it moves through the layers of the wall. In the latter embodiments, the tissue-penetrating element may be part of the impedance measurement system and may incorporate a tissue securement element, and the target depth of deployment may range from an inner layer, such as the muscularis of a stomach, to the full thickness of the wall.

In one or more additional preferred embodiments, methods and devices are disclosed for safely and reliably penetrating or securing the wall of a hollow organ without endangering surrounding structures. In one series of embodiments, methods and devices are described wherein the wall of the hollow organ is engaged and pulled into its lumen in order to create a safety gap between the outer surface of the organ and surrounding structures, and a tissue device such as a tissue penetrating element or securing element is deployed to safely penetrate the wall without extending beyond the safety gap. In an additional series of preferred embodiments, electrical impedance may be used to guide the deployment of the tissue-penetrating element, with or without creation of a safety gap. In the case where a safety gap is not created, the tissue impedance measurement system may be configured to provide feedback when the tip of the tissue penetrating element has passed through the outermost wall layer, thereby allowing the operator, or an automatic deployment system, to stop further deployment. In at least one preferred embodiment of the aforementioned methods and devices for safely and reliably penetrating the wall of a hollow organ are applied to a stomach where the methods manipulate the mucosa prior to deployment of a tissue-penetrating element or securement mechanism to improve the predictability of the overall thickness of the stomach wall. In a further preferred embodiment, the methods and devices described may be used to pass not only a securement device through the wall, but also devices such as electrodes, anchoring devices, implantable devices, or conduits for fluids, materials or other devices.

In yet another group of preferred embodiments of the invention, methods and devices are described for approximating two or more regions of a wall of a hollow organ. In at least one preferred embodiment for a stomach organ, the muscularis wall layer is selectively engaged in two or more regions using the methods and devices described previously, and then the regions are pulled together. In another preferred embodiment, the walls are pulled into the lumen to create a safety gap to allow safe and reliable deployment of securement elements through the wall where the securement elements are then pulled together to approximate the regions. In another embodiment, the walls are approximated and then pulled into the lumen to create a safety gap prior to deployment of a securement element through both regions of the wall.

Other preferred embodiments of the present invention relate to methods and devices for performing gastroplasty procedures. Specific methods and devices are described for safe and reliable engagement, approximation and securement of regions of the stomach wall to create a gastric pouch or partition, using combinations of the methods and devices described previously. In at least one embodiment, methods and devices are disclosed for performing endoluminal gastroplasty using a device configured to pass through the esophagus and enable the steps of engagement, approximation and securement of the anterior and posterior walls of the stomach to create a gastric partition. In at least one embodiment of the aforementioned methods and devices, the device comprises a pair of hinged effectors, each of which is configured to manipulate the mucosa, the innermost wall layer in an exemplary organ, the stomach and selectively engage the muscularis, the next wall layer in the exemplary organ, the stomach at two regions of the wall, and then approximate the two regions and safely and reliably deploy a full-thickness securement element through the two regions. In one variant of this embodiment, a biocompatible material may be used to reinforce the sites of securement of the approximated regions of the wall. In a specific method for using the aforementioned device to create a more substantial gastric pouch with a small restrictive outlet to delay the passage of material or fluid through the organ's lumen, the device is used to create a first partition and then a second partition adjacent to the first. In another group of related preferred embodiments, a device is described which incorporates a stitching mechanism, and methods are disclosed for using this device to create a luminal partition or pouch, with or without a restrictive outlet. A further preferred embodiment describes a method of combining the hinged-effector device with the stitching device to create a luminal pouch with a restrictive outlet.

In another preferred embodiment of the invention, a device is disclosed which employs a biocompatible material for attachment between the anterior and posterior walls of an organ to create a partition, which may be useful in the treatment of obesity or GERD in a stomach organ, and which may or may not incorporate a restrictive outlet. A method is also described for attaching the biocompatible material to the organ wall.

In another series of preferred embodiments, methods and devices are described for creating an effective and durable restrictive outlet to a luminal pouch, in order to delay/restrict flow through the luminal pouch, as is desired in the case of an anti-obesity procedure, or to restrict the reflux of a stomach's contents from the pouch, as is desired in the case of a GERD treatment. In one preferred embodiment, a method and device are disclosed for gathering and bunching together excess innermost wall layer segments in the vicinity of the desired outlet, and securing the bunched layer segments so as to at least partially block the flow of material or fluid through the outlet. In another series of preferred embodiments, an object is attached to the organ wall to create a restrictive outlet, which may be adjustable. In yet another embodiment, a method is disclosed for bulking the region of a luminal pouch outlet so as to create a restriction. In one or more additional preferred embodiments, methods and devices are describe for forming a tubular extension of the luminal pouch so as to create a restriction to flow, wherein the restrictive effect may be increased or decreased by lengthening or shortening the extension, respectively, or by adding or removing pleats along the length of the extension, all of which may be done endoscopically to adjust the restrictive effect as desired. In still another preferred embodiment, methods and devices are disclosed for forming a restrictive outlet to a luminal pouch by modifying the properties of the organ wall tissue in the vicinity of the desired outlet.

In another group of preferred embodiments, methods are disclosed for treating the walls of the stomach in the vicinity of a gastric pouch and restrictive outlet to minimize the amount of dilation that may occur. Such methods include modifying the properties of the stomach wall so as to create scarification or shrinkage of the tissue layers.

For purposes of summarizing the preferred embodiments of the invention and the advantages achieved over the prior art, certain objects and advantages have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the present invention herein disclosed. These and other embodiments of the present invention will become readily apparent to those skilled in the art from the following detailed description of the preferred embodiments having reference to the attached figures. The invention is not limited to any particular preferred embodiment(s) disclosed.

BRIEF DESCRIPTION OF DRAWINGS

Having thus summarized the general nature of the invention, certain preferred embodiments and modifications thereof will become apparent to those skilled in the art from the detailed description herein having reference to the figures that follow, of which:

FIGS. 4a-b are section views illustrating the steps of for manipulating the mucosal surface of the stomach;

FIGS. 5a-b are section views illustrating the steps of selectively engaging the muscularis of the stomach;

FIG. 11 is a schematic view of another aspect of the device of FIG. 9;

FIG. 11a is an enlarged view of a portion of the device of FIG. 9 at line 9a;

FIG. 12 is a schematic illustration of an arrangement of the mechanisms within the device of FIG. 9;

FIG. 13 is a section view taken through line A-A of FIG. 8 demonstrating initial positioning of the device of FIG. 9 within the lumen of the stomach;

FIG. 13a is an enlarged view of one of the hook needles, showing its slightly retracted and un-deployed position in the configuration of the device as shown in FIG. 13;

FIG. 14 is a section view taken through line A-A of FIG. 8 demonstrating the device in relation to the lumen of the stomach after the lumen has been evacuated;

FIG. 14a is an enlarged view of one of the hook needles, showing its slightly retracted and un-deployed position in the configuration of the device as shown in FIG. 14;

FIG. 15 is a section view taken through line A-A of FIG. 8 demonstrating the opening of the device and engagement of the mucosa;

FIG. 15a is an enlarged view of one of the hook needles, showing its slightly retracted and deployed position in the configuration of the device as shown in FIG. 15;

FIG. 16 is a section view taken through line A-A of FIG. 8 demonstrating closing of the device to stretch out the mucosa around the body of the device;

FIG. 16a is an enlarged view of one of the hook needles, showing its slightly retracted and deployed position in the configuration of the device as shown in FIG. 16;

FIG. 19 is a section view taken through line A-A of FIG. 8 demonstrating closure of the device to approximate the engaged regions of the wall;

FIG. 20 is a section view taken through line A-A of FIG. 8 demonstrating advancement of a securement element through the approximated walls of the stomach;

FIG. 21 is a section view taken through line A-A of FIG. 8 demonstrating the securement element in place through the approximated walls of the stomach;

FIG. 22a is a section view of the stomach shown in FIG. 22, taken through line 22a-22a;

FIG. 30 is a perspective view of a suture deployment device, shown attached to the end of a flexible endoscope;

FIG. 31 is a section view of the suture deployment device of FIG. 30, showing the needle deployment arm ready to push the needle;

FIG. 31a is a detail view of a needle useful in a suture deployment device;

FIG. 33 is a section view of the suture deployment device of FIG. 30, showing the needle deployment arm ready to retract the needle;

FIG. 41 is a side section view showing a suture deployment device adapted to measure tissue impedance;

FIG. 49 is a section view showing the endoscopic device of FIG. 47 showing the mucosa spread;

FIG. 50 is a section view showing the endoscopic device of FIG. 47 fully open and preparing to engage the muscularis;

DETAILED DESCRIPTION

Figure 1:
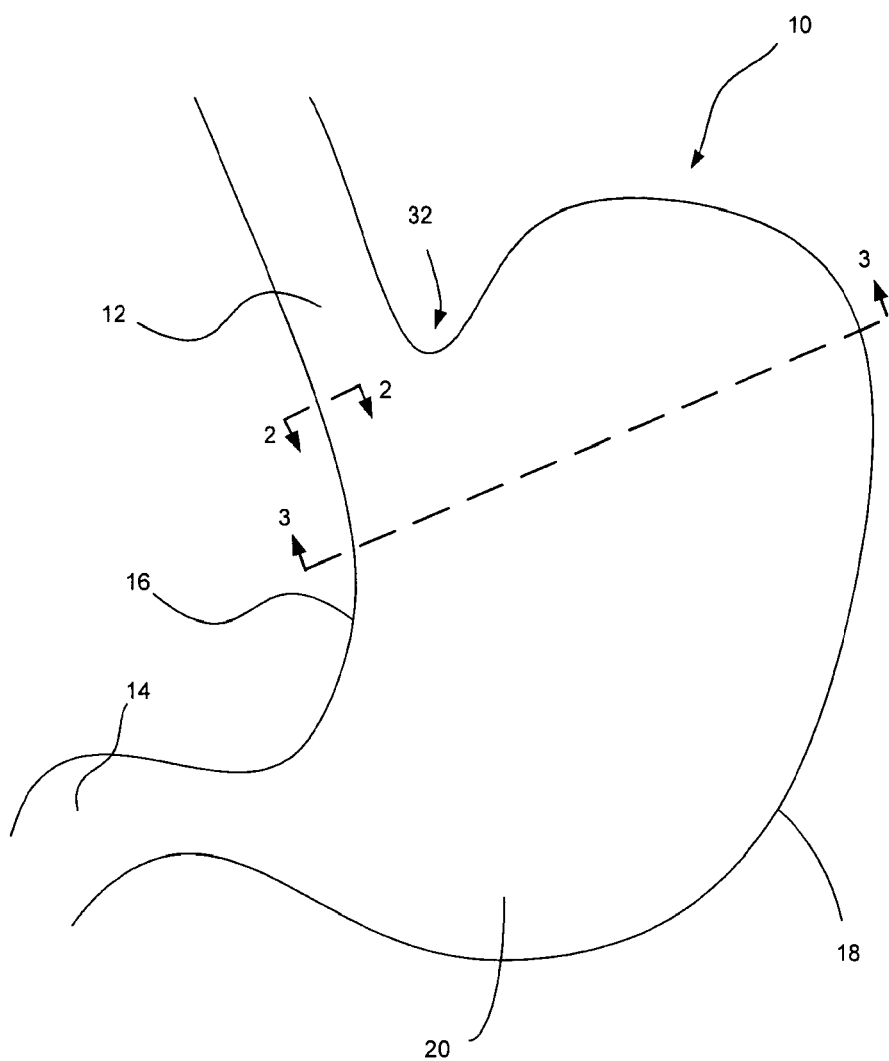
FIG. 1 is an anterior schematic view of an exemplary luminal organ, a stomach.
Figure 2:
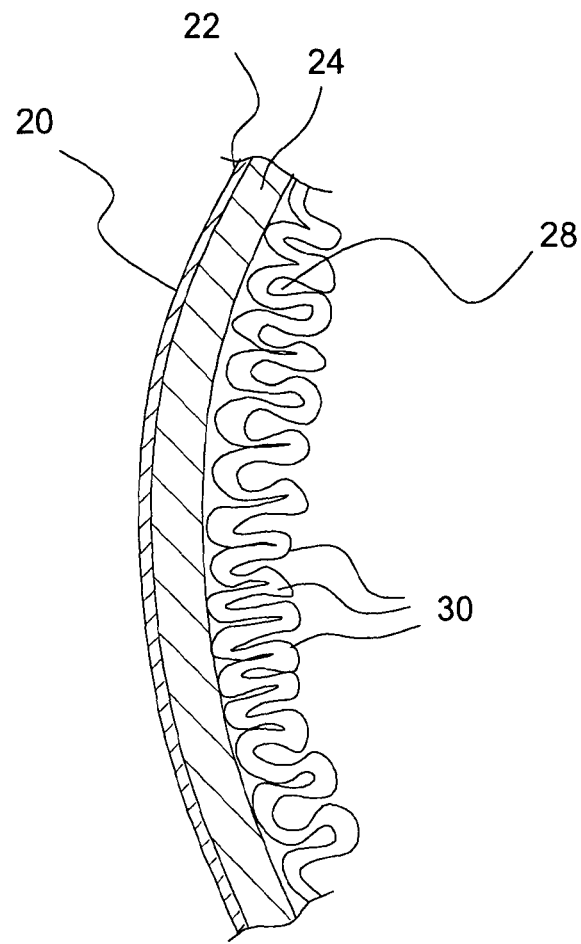
FIG. 2 is a section view of the stomach wall taken through line 2-2 of FIG. 1.
Figure 3:
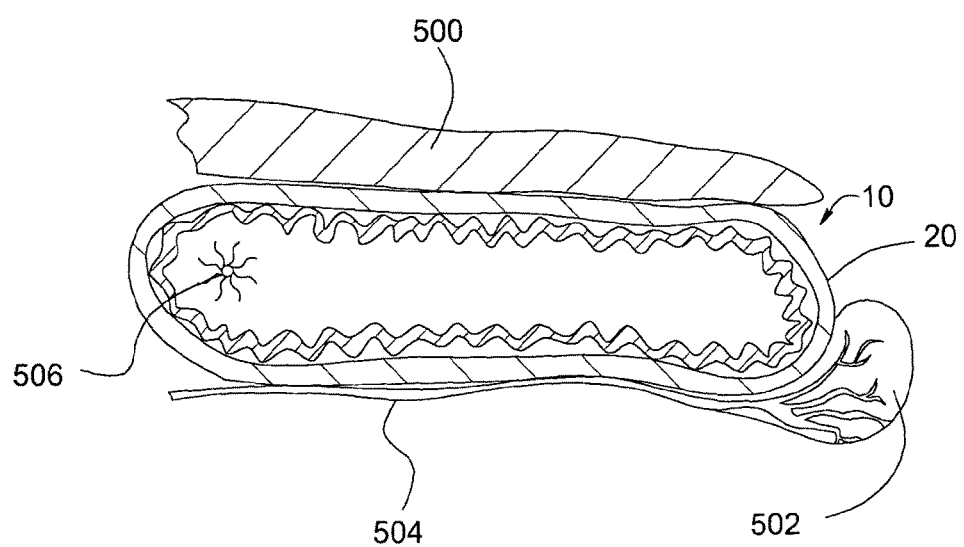
FIG. 3 is a section view of the stomach and surrounding anatomy taken through line 3-3 of FIG. 1.

The present invention relates to endoluminal therapy and particularly to methods and devices for manipulation of the walls of luminal organs such as the stomach. Before describing embodiments of the devices and methods of the invention, an exemplary luminal organ, a stomach 10 will first be described in more detail. It is understood that the method and devices of the present invention may be applied to any luminal organ. Application of the present invention a stomach 10 is thus for illustrative purposes only. FIGS. 1, 2 and 3 illustrate a representation of the normal anatomy of a stomach 10.

As shown if FIG. 1, the exemplary luminal organ, the stomach 10 includes an upper opening at the esophagus 12, an Angle of His 32 at the junction between esophagus 12 and stomach 10, and a lower opening at the pylorus 14 which communicates with the small intestine (not shown). For reference, the stomach 10 further includes a lesser curvature 16 and a greater curvature 18 as well as posterior and anterior stomach walls 20. This organ, the stomach wall 20 comprises three major layers (shown in cross-section in FIG. 2): an outermost layer, the serosa 22, the muscularis 24 and the innermost layer, the mucosa 28. (For simplicity, sub-layers such as the sub-mucosa, muscularis propria, muscularis mucosae and others have been grouped together within the appropriate major layers and are therefore not discussed independently.) In a normal, undistended stomach 10, the innermost layer, the mucosa 28 is loosely attached to the next wall layer, the muscularis 24 and typically forms numerous rugal folds or rugae 30.

FIG. 3 is a cross-section of the stomach 10 of FIG. 1 taken at line 3-3, showing typical surrounding anatomy such as the liver 500, spleen 502 and splenic artery 504. The lower esophageal sphincter 506 has also been shown to provide perspective.

The deployment of securement elements through wall 20 is a key part of many endoluminal procedures such as gastroplasty. For such securement elements to provide durable securement, they may need to be placed through the full thickness of stomach wall 20, including the outermost layer, the serosa layer 22. It will be appreciated that the variable nature of rugae 30 makes the overall thickness of a given region of stomach wall 20 relatively unpredictable. Therefore, to reliably deploy a securement element via a tissue device from within the lumen completely through organ wall 20 requires the securement element to be deployed to a depth which takes into account the maximum thickness of wall 20, which occurs when the maximum number and size of rugae 30 are encountered during deployment. As such, the deployment of such securement elements may significantly overshoot the outer surface of serosa 22, except in cases when the maximum thickness of wall 20 is encountered. Because damage to organs surrounding the stomach such as the liver 500 and spleen 502 and puncture wounds to vessels such as the splenic artery 504 may result in significant morbidity, it will be appreciated that consideration of such surrounding anatomy is of paramount importance when penetrating an organ wall. Many aspects of the present invention relate to endoluminal procedures that are directed at minimizing this risk.

FIGS. 4a and 4b shows a depiction of a method and device for reducing the risk described above. In FIG. 4a a section of stomach wall is shown, along with an innermost wall, mucosal manipulation mechanism 508. For simplicity, stomach wall 20 is shown as a single layer plus the rugae 30, without detailing the muscularis and serosa. This simplification is carried throughout most of the drawings disclosed hereafter. Mucosal manipulation device 508 comprises a pair of mucosal engagement mechanisms 510 having tissue engagement hooks 512. In a typical application of device 508, hooks 512 would be brought into contact with the innermost wall layer, the mucosa 28, and then spread apart to stretch out this layer, the rugae 30 and thereby leave a single, flattened innermost wall layer of mucosa 28 adjacent device 508, as shown in FIG. 4b.

In FIG. 5a, a tissue device, in particular a tissue engagement mechanism 514 is shown pressed against the flattened innermost wall layer, the mucosa 28 created by the procedure shown in FIGS. 4a and 4b. Mechanism 514 has a hook needle 58 mounted on a rotating element that may be a spur gear 68. When spur gear 68 is rotated, needle 58 is deployed to selectively engage muscularis 24, as shown in FIG. 5b. The selectivity of the engagement of the layer adjacent the innermost layer, the muscularis 24 is the result of properly dimensioning hook needle 58 in combination with the relative predictability of a single layer of flattened mucosa 28.

Figure 6A:
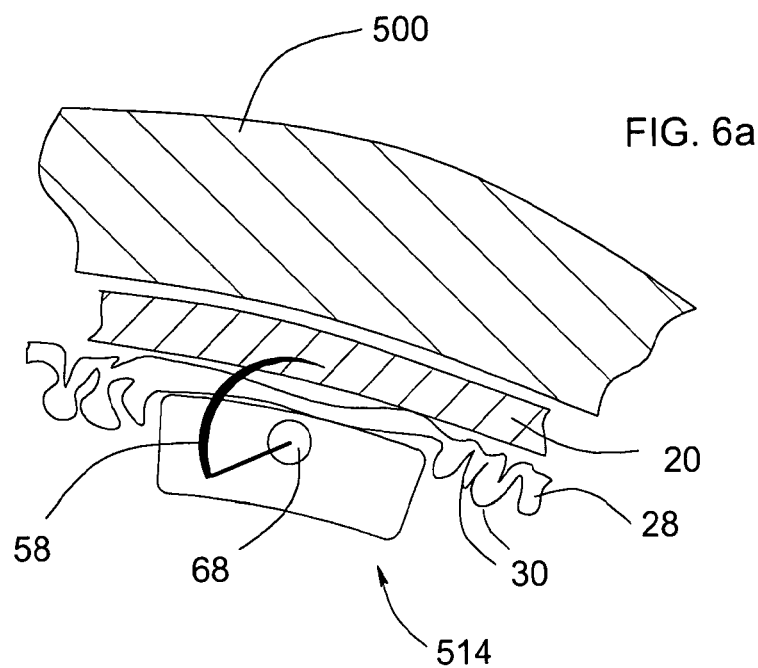
FIGS. 6a-b are section views illustrating the steps of pulling the stomach wall into the lumen of the stomach and creating a gap between the stomach wall and surrounding anatomy.
Figure 6B:
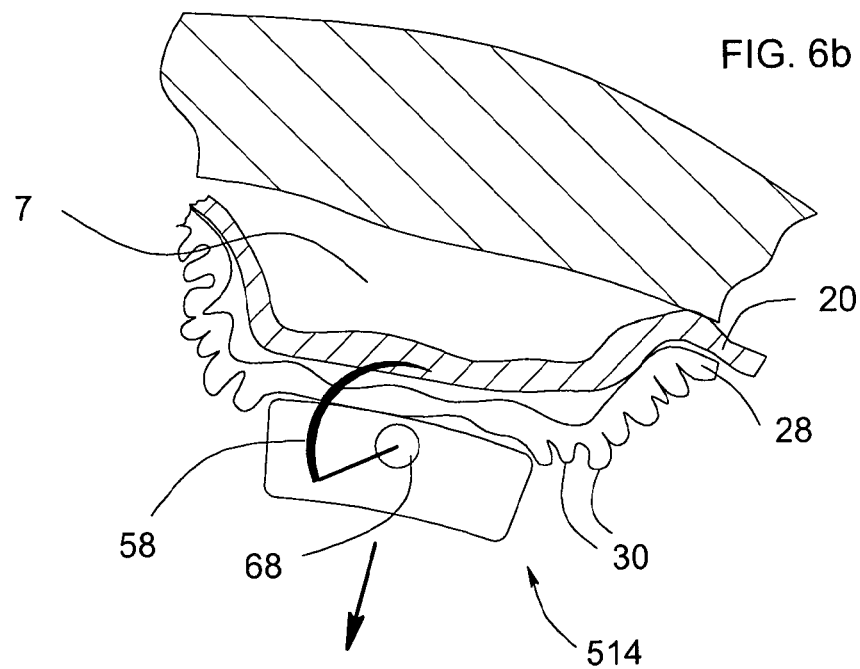

FIGS. 6a and 6b carry forth the elements shown in FIG. 5b, with the addition of an adjacent organ, the liver 500. In FIG. 6b, mechanism 514 has been moved into the lumen of stomach, pulling wall 20 along with it, and thereby creating a safety gap 7 between the outer surface of wall 20 and liver 500. As shown, the depth and steepness of the sides of gap 7 are such that the adjacent organ, the liver 500 does not conform with, and thereby fill in, gap 7.

Figure 7A:
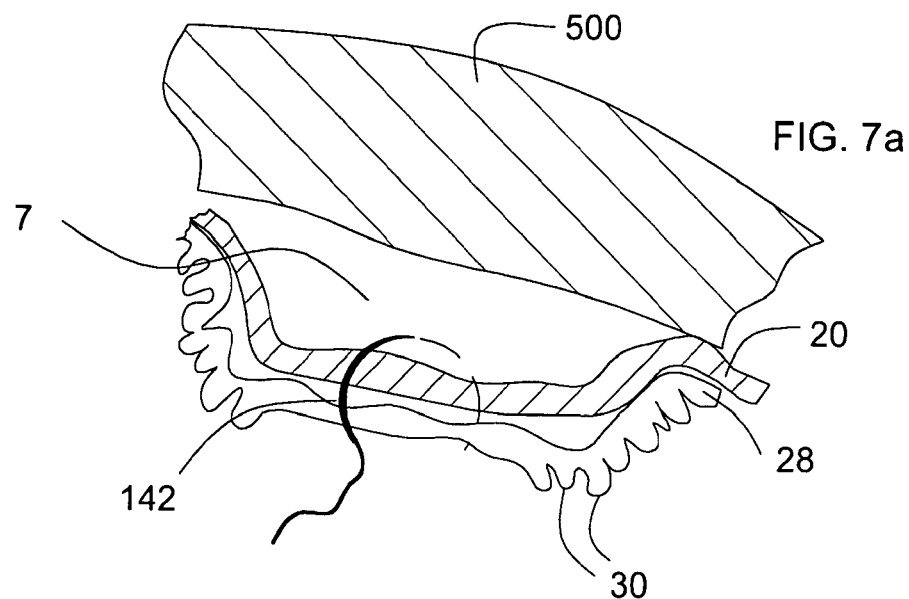
FIGS. 7a-b are section views illustrating the deployment of securement devices through the stomach wall into the safety gap, with 7a showing a curved suture and 7b showing a hollow needle deploying a T-anchor.
Figure 7B:
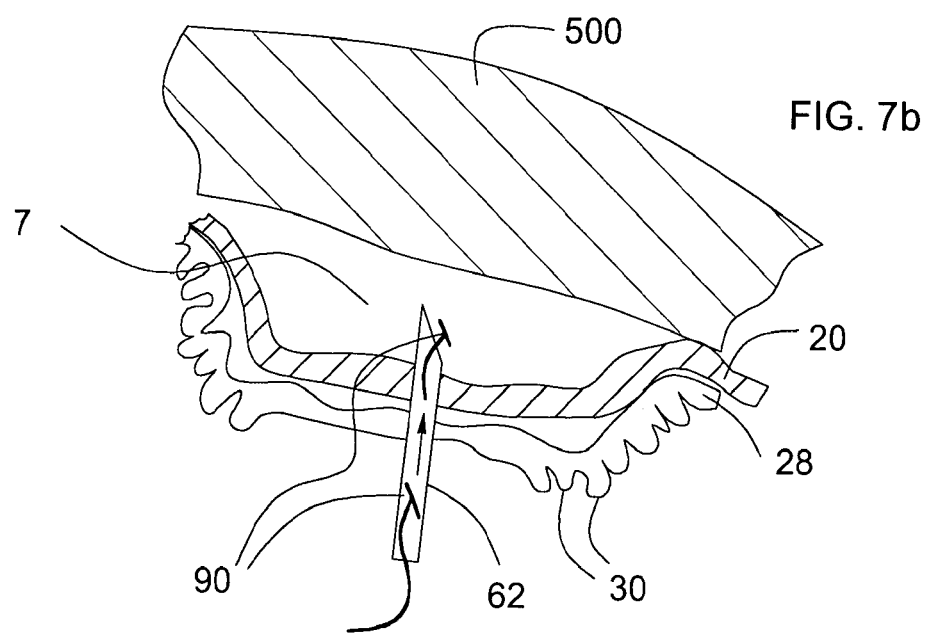

FIGS. 7a and 7b carry forth the scenario shown in FIG. 6b, illustrating the deployment of securement devices through wall 20 into the gap 7. For purposes of clarity, mechanism 514 is not shown, but it will be appreciated that it must maintain tension on wall 20 to sustain gap 7. FIG. 7a shows curved suture needle 142 passing through the full thickness of wall 20, into gap 7 and back into wall 20 without contacting the liver 500. Similarly, FIG. 7b shows a hollow needle 62 passing through wall 20 and deploying a thread 64 having a T-anchor 90 on its end.

Figure 8:
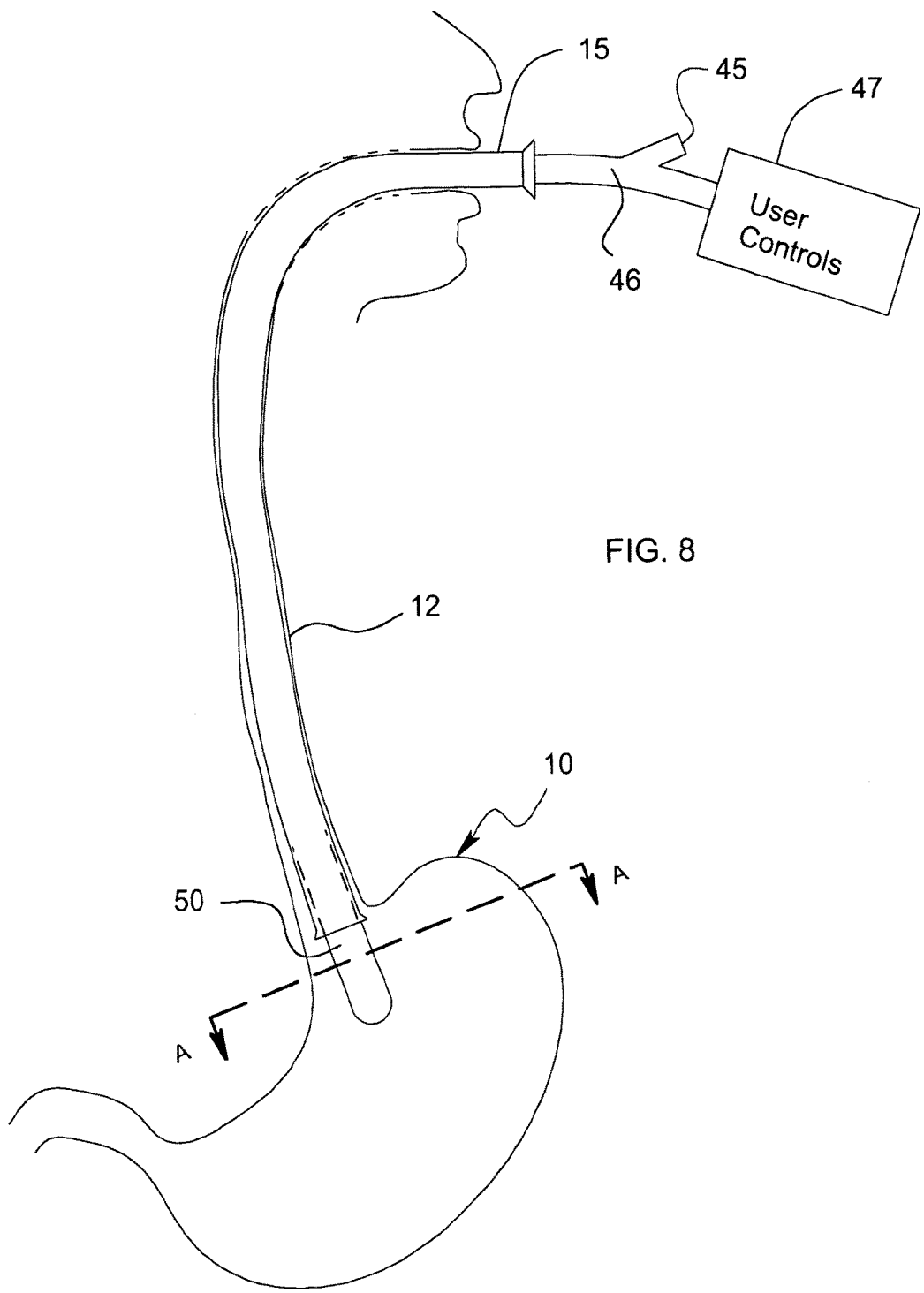
FIG. 8 is a schematic illustration of a trans-esophageal device being inserted into a patient's stomach.

FIG. 8 shows a trans-esophageal device 50 which is designed to perform at least a portion of the methods described thus far, such methods including manipulation of the innermost wall layer, the mucosa to flatten out its (rugal) folds, selective engagement of another wall layer, the muscularis, approximation of two regions of the stomach wall, pulling such approximated regions into the lumen to create a safety gap, and deploying a plurality of securement elements through the approximated tissue regions to permanently secure them.

Device 50 is shown in FIG. 8 being inserted into a patient's stomach 10 through esophagus 12. In the scenario shown, device 50 is inserted through an optional overtube 15, which would normally be inserted into esophagus 12 first and would serve to shield the wall of esophagus 12 from abrasion damage during the passage of a large instrument such as device 50. Device 50 may be attached to the end of a flexible endoscope 46, in which case an auxiliary conduit (not shown) running from device 50 alongside endoscope 46 and out the patient's mouth will be required in order to accommodate the multitude of control cables needed to operate device 50. Flexible endoscopes typically have an access channel 45, through which instruments can be passed, and user controls such as steering knobs, suction valves, insufflation, which are inferred by user control block 47. It will be appreciated that device 50 may be configured as a stand-alone device, that is, not mounted onto an endoscope, in which case the user controls 47 and the auxiliary conduit (not shown) may be incorporated into a single device 50.

Figure 9:
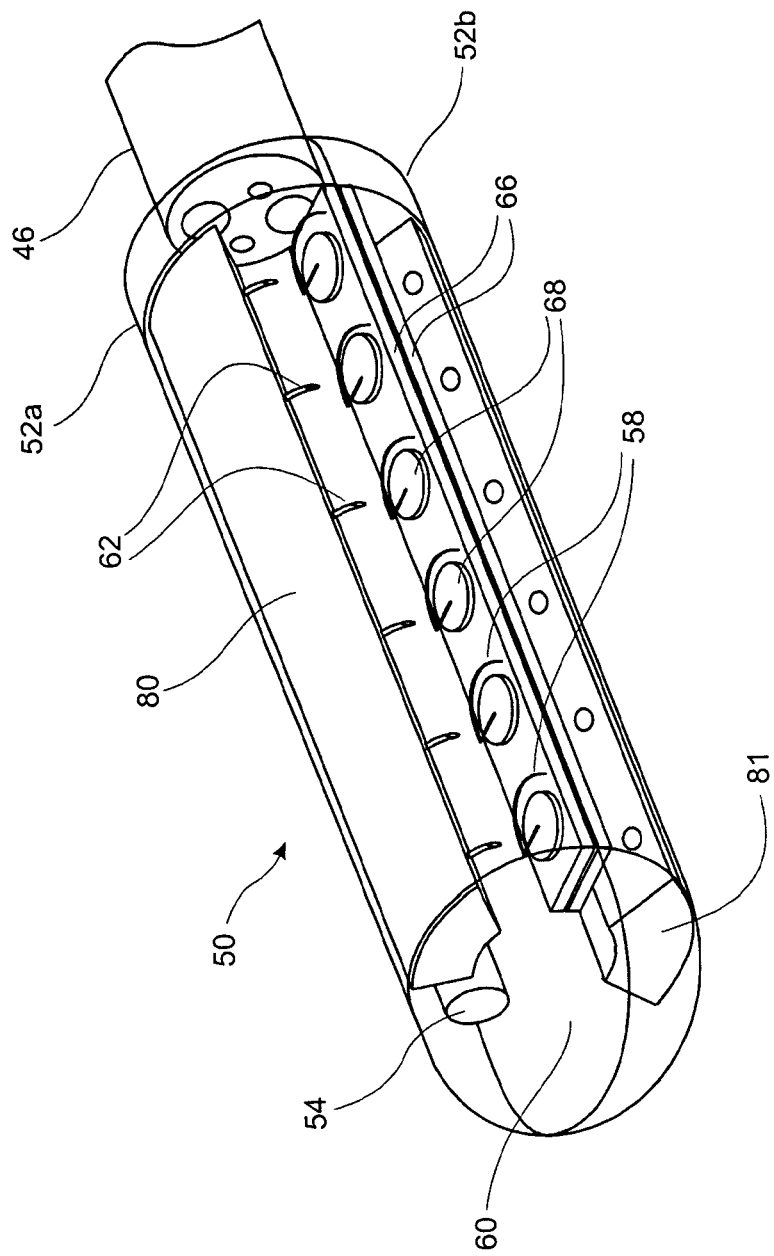
FIG. 9 is a perspective view of a trans-esophageal device configured to secure two regions of the stomach wall together.
Figure 10:
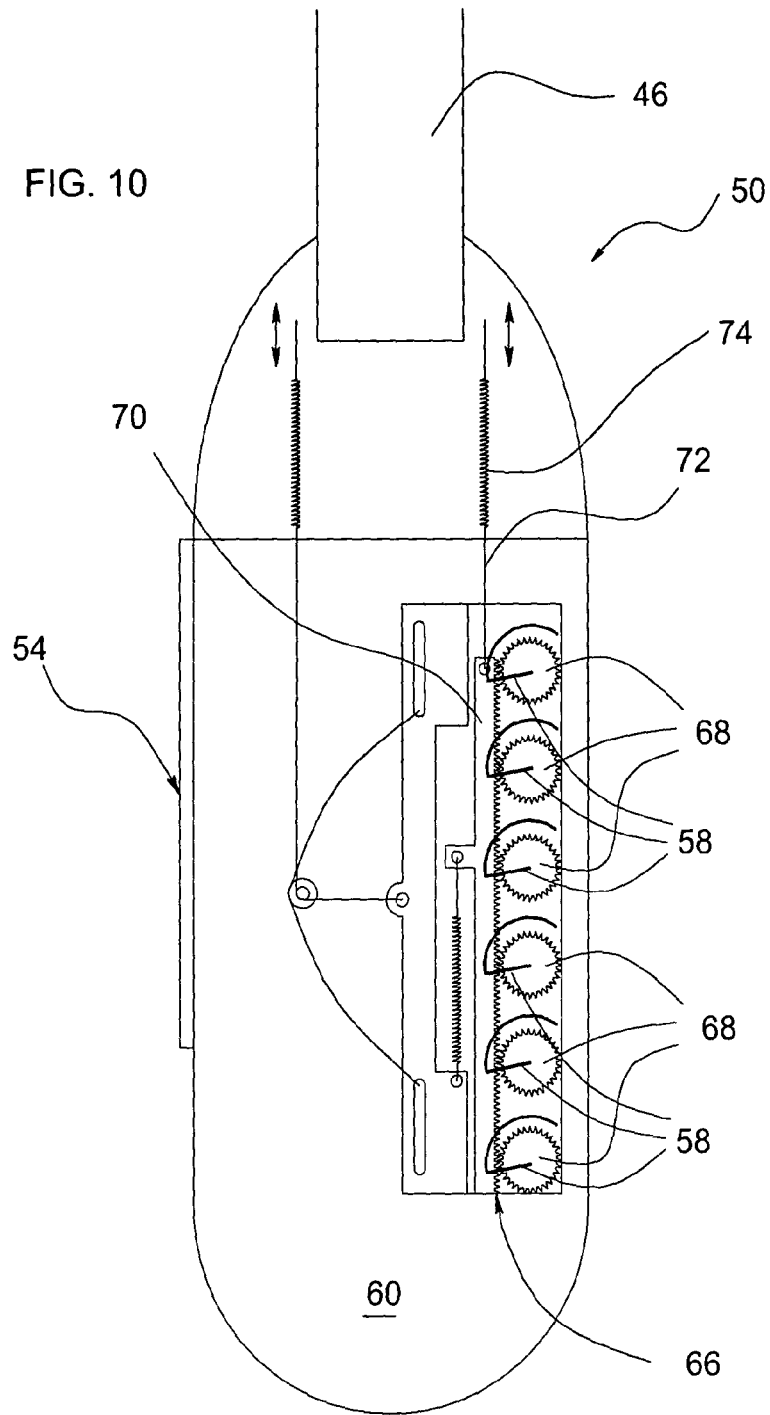
FIG. 10 is a schematic view of another aspect of the device of FIG. 9.

FIG. 9 shows a perspective view of trans-esophageal device 50, mounted on the end of endoscope 46. The device is configured with a rounded cylindrical shape having a top half 52a and a bottom half 52b, the two halves meeting at seam 79, pivotally linked by hinge 54 and openable along edge 56, shown in the closed state. Top half 52a includes an array of securement elements, in this case six suture deployment needles 62, moveable together in carriage block 80, and an array of tissue engagement mechanisms moveable in carriage 66. Bottom half 52b also contains an array of tissue engagement mechanisms moveable in carriage 66, and has a needle catcher 81.

In the embodiment shown in FIG. 6, tissue engagement and drawing mechanisms in the form of hook-shaped needles 58 are shown. As illustrated, a plurality of hook needles 58 may be mounted on spur gears 68 which may engage a linear rack 70 which may be attached to an actuating wire 72. The hook needles 58 may be deployed by pulling the wire 72, thereby drawing the rack 70 upwards, and causing the spur gears 68 to rotate (clockwise as shown) such that the needles 58 engage the tissue of a stomach wall 20. A release spring 74 is generally provided to bias the rack 70 in a direction to allow the hook needles 58 to be removed from the stomach wall 20. Hook needles 58 preferably have a sharp tip to penetrate the tough tissue of the muscularis, but a generally flat body so as to engage the tissue without ripping through it, after the needles have been deployed.

Hook needles 58 are mounted on carriage 66, which can be retracted toward hinge 54 or advanced toward edge 56 by pulling on, or relaxing, wire 86. As will be described in more detail in FIGS. 13-18, by adjusting the position of carriage 66, the hook needles 58 can selectively engage the innermost wall layer, the mucosa 28 or the next wall layer muscularis 24 of stomach wall 20. Once engaged, the carriage 66 may be retracted into the cavity 60 of the device 50, thus capturing a portion of stomach wall 20 into the cavity 60. Device 50 is configured to allow both top half 52a and bottom half 52b to capture portions of stomach wall 20 with the two halves hinged apart, then to approximate the two portions of stomach wall 20 as the halves are brought together.

Securement devices or tissue devices for securing the portions of captured stomach walls 20 together are illustrated in FIG. 11. As shown, the device 50 includes a plurality of suture deployment needles 62 which comprise substantially hollow tubes configured to carry sutures 64. The suture needles 62 may be advanced by pulling on wire 86. In the embodiment shown, the suture needles 62 are held in a carriage block 80 that incorporates an angled slot 83. A pin 84 attached to wire 86 is configured to travel in a constrained straight slot 88 (which is integral to half 52a) as well as in angled slot 83. As the wire 86 is pulled, pin 84 moves through straight slot 88, forcing angled slot 83 to follow the path of pin 84 and thereby advancing the needle carriage 80 toward the front edge 56 of device 50. Likewise, when wire 86 is released, needle carriage 80 is retracted by spring 76 disposed such that pin 84 will be biased towards the spring end of slot 88, thereby causing the needle carriage 80 to be retracted. Alternatively one or more springs may be provided in different orientations and/or positions in order to retract the suture needle carriage 80. Alternatively, one or more retraction wires may be provided to allow a clinician to actively pull the carriage 80 in order to retract the suture needles 62 from the tissue. Still other pull wire and cam combinations may be employed to achieve the desired deployment of the suture needles 62. For example, the needle carriage 80 may comprise one or more wedge-shaped surfaces configured to engage a cam pulled by an actuating wire. Alternatively, each suture needle 62 may be located on an individual carriage block, thus allowing each needle 62 to be deployed individually if so desired.

Figure 11A:
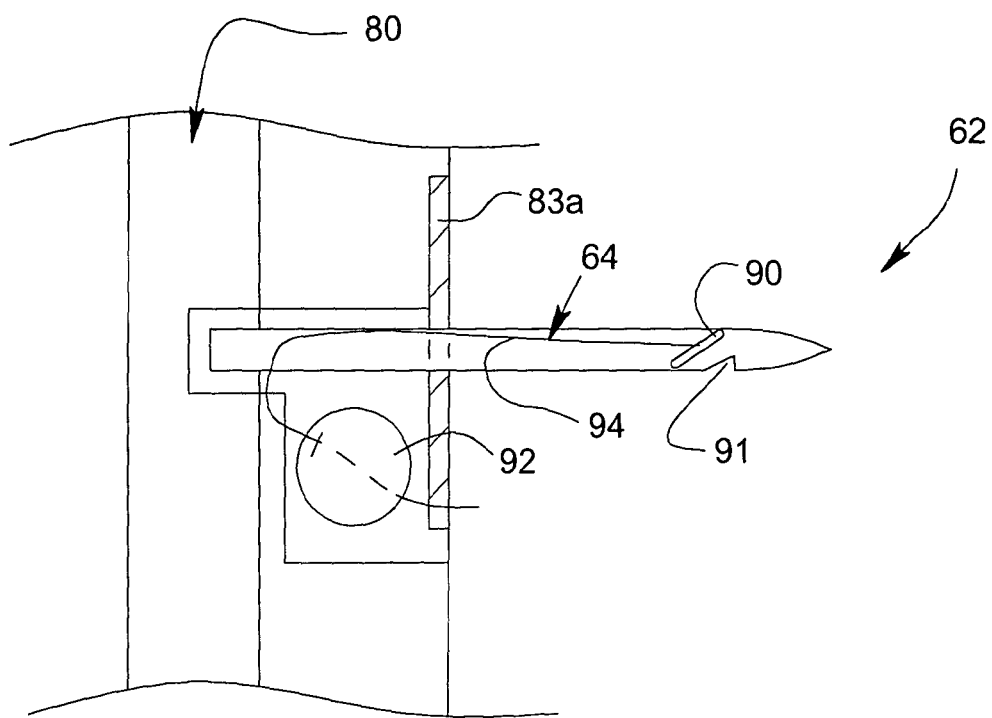

With reference to FIG. 11*a*, the securement device may comprise one or more sutures 64 comprising T-anchors 90 and/or ball anchors 92 joined by a thread 94. The thread 64, T-anchors 90, and ball anchors 92 may be made of any suitable bioabsorbable or biocompatible material available. Alternatively, staples or other slightly more rigid securement structure may be used.

FIG. 12 illustrates an exemplifying arrangement of the hook needles 58, the hook needle carriage 66, the suture needles 62, and the suture needle carriage 80 as arranged in one of the device halves 52*a*. It will be appreciated that the number and arrangement of suture needles 62 is flexible, and may be adapted for a specific purpose. In the embodiment shown, the numbers of suture needles 62 were chosen to provide reasonably close spacing of sutures along the segment of secured stomach wall tissue. The length of device 50, and thus the length of the secured segment of stomach wall tissue, was chosen to be roughly the maximum length which can be passed around the bend between the oral cavity and the esophagus, which is generally between about 1.5 and 2.5 inches, depending on the shape of the device and the anatomy of the patient. Similarly, the diameter of device 50, in its closed configuration was chosen to be the maximum allowable through a typical esophagus, which is roughly between about 0.5 and 0.75 inches.

FIG. 13 is a section view taken through line A-A of FIG. 8 demonstrating the initial positioning of device 50 in its closed position within the lumen of an organ, stomach 10. Device 50 as illustrated has been simplified for clarity, showing only hinge 54, halves 52*a* and 52*b*, and carriages 66. FIG. 13*a* shows the position of distal-most spur gear 68 and hook needle 58 on carriage 66 in relation to the front edge 56 of device 50 in the arrangement shown in FIG. 13. As illustrated, carriage 66 is slightly retracted and needle 58 is in its un-deployed position in the configuration of the device as shown in FIG. 13.

FIGS. 14 and 14*a* are identical to FIGS. 13 and 13*a*, except the lumen of stomach 10 has been evacuated such that organ wall 20 is brought into close contact around device 50.

FIG. 15 shows the device 50 of FIG. 14 with hinge 54 opened and hook needles 58 deployed to engage the innermost wall layer, the mucosa. FIG. 15*a* shows that carriage 66 is still slightly retracted and needle 58 is in its deployed position.

FIG. 16 shows the device 50 of FIG. 15 with hinge 54 closed and hook needles 58 still engaging the mucosa, thereby stretching the mucosa 28 over the body of device 50. FIG. 16*a* shows that carriage 66 is still slightly retracted and needle 58 is still in its deployed position. The operation shown in FIGS. 15 and 16 may be repeated multiple times to ensure that all of the rugal folds 30 are substantially flattened in the vicinity of device 50. Although it is not shown, it will be understood that once halves 52*a* and 52*b* are closed and the mucosa 28 has been stretched, hook needles 58 are retracted before halves 52*a* and 52*b* are opened again.

As an alternative to the method of flattening the rugal folds 30 as demonstrated in FIGS. 15 and 16, device 50 may include one or more tissue manipulation mechanisms or tissue engaging members such as pawl teeth oriented such that as halves 52*a* and 52*b* are opened, the teeth will slide past the rugal rugae 30, but as the device 50 is closed, the teeth will engage the mucosa 28, thereby pulling the rugae 30 toward the front edge 56 of the device 50. Alternatively, the device 50 may be configured such that the gripping and pulling action is performed as the device 50 is opened.

Figure 17:
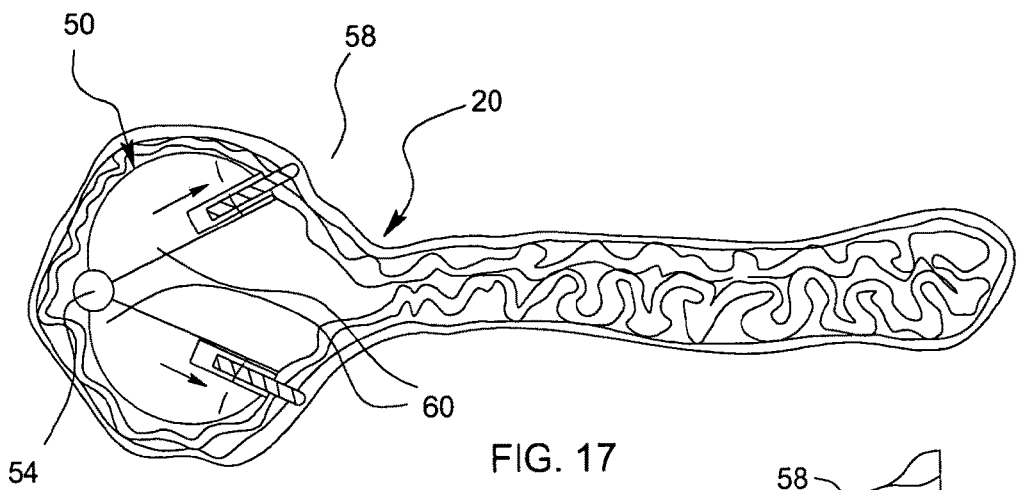
FIG. 17 is a section view taken through line A-A of FIG. 8 demonstrating the opening of the device and engagement of the muscularis.
Figure 17A:
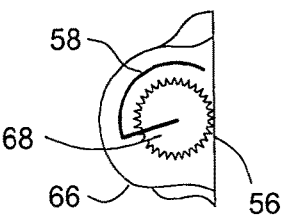
FIGS. 17a-b show an enlarged view of one of the hook needles, showing in 17a its un-retracted and un-deployed position, and in 17b its un-retracted and deployed position as shown in FIG. 17.
Figure 17B:
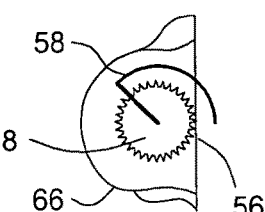

FIG. 17 shows the device 50 of FIG. 16 with hinge 54 once again open and hook needles 58 deployed to selectively engage another wall layer, the muscularis 24 of stomach wall 20. FIG. 17*a* shows that carriage 66 has been advanced to the edge 56 of device 50 so that when the needle is deployed, as shown in FIG. 17*b*, the stroke of needles 58 penetrate more deeply into the wall, in the case shown into the muscularis.

Figure 18:
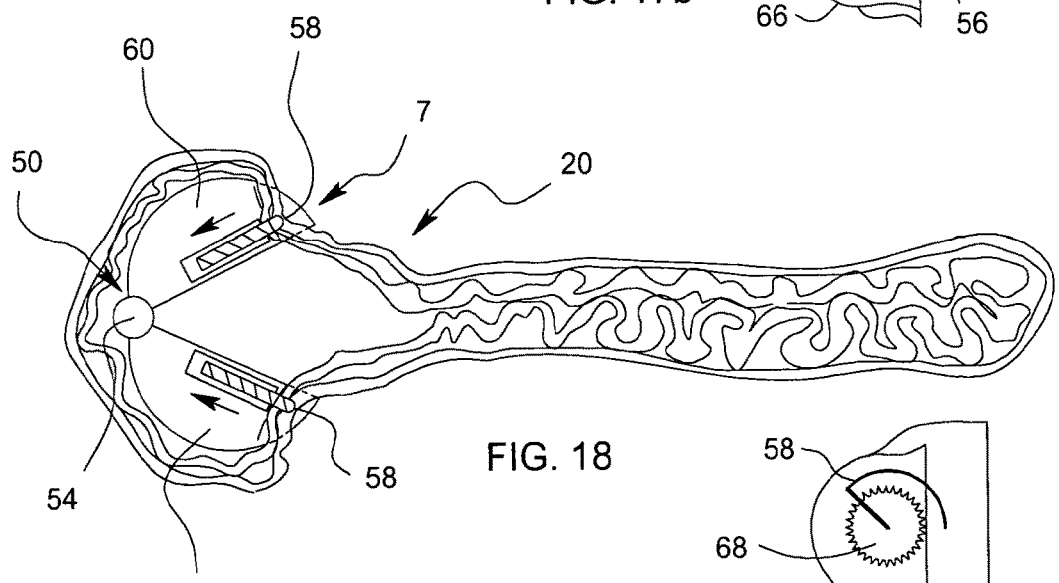
FIG. 18 is a section view taken through line A-A of FIG. 8 demonstrating retraction of the engaged walls into the lumen of the stomach.
Figure 18A:
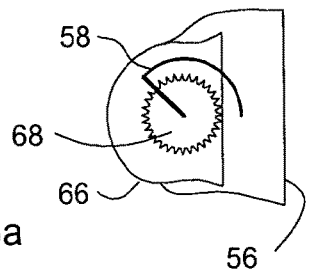
FIG. 18a is an enlarged view of one of the hook needles, showing its fully retracted and deployed position in the configuration of the device as shown in FIG. 18.

FIG. 18 shows the device 50 of FIG. 17 with needles 58 still engaging the muscularis 24 while carriage 66 is retracted, as shown in FIG. 18*a*. In this way, a portion of the engaged segments of anterior and posterior stomach wall 20 are pulled into cavity 60 of device 50, and a safety gap 7 is created outside stomach wall 20.

FIG. 19 shows the device 50 of FIG. 18 with hinge 54 closed and halves 52*a* and 52*b* brought together such that the engaged portions of stomach wall 20 are approximated. Note that safety gap 7 is further enhanced with device 50 in the closed position. Also shown in the Figure are needle deployment carriage 80 with needles 62, and needle catcher 81. Although not detailed elsewhere, it will be appreciated that needle catcher 81 may be activated in the same manner, and at the same time as, deployment carriage 80.

As shown in FIG. 20, deployment carriage 80 is activated to push needles 62 through the captured segments of stomach wall 20, while simultaneously needle catcher 81 is forced toward the bottom side of the captured wall 20 in order to receive the hollow needles 62 coming through wall 20.

FIG. 21 shows the completed securement procedure, with both the deployment carriage 80 and needle catcher 81 having been retracted, and needles 62 being captured by the needle catcher 81. As will be evident by the combination of FIGS. 11*a* and 21, as the hollow needles 62 pass through the tissue and into needle catcher 81, an array of latches in needle catcher 81 (not shown) engage notches 91 near the tips of each of hollow needles 62, thereby allowing needle catcher to engage needles 62 and pull them through the captured stomach wall 20. As this happens, each ball anchor 92 of suture elements 64 become anchored against the top surface of the stomach wall 20 captured in half 52*a*. When needle catcher 81 is retracted, hollow needles 62 are pulled off of suture elements 64, exposing T-anchors 90 and allowing them to become anchored against the bottom surface of the stomach wall 20 captured in half 52*b*.

Figure 22:
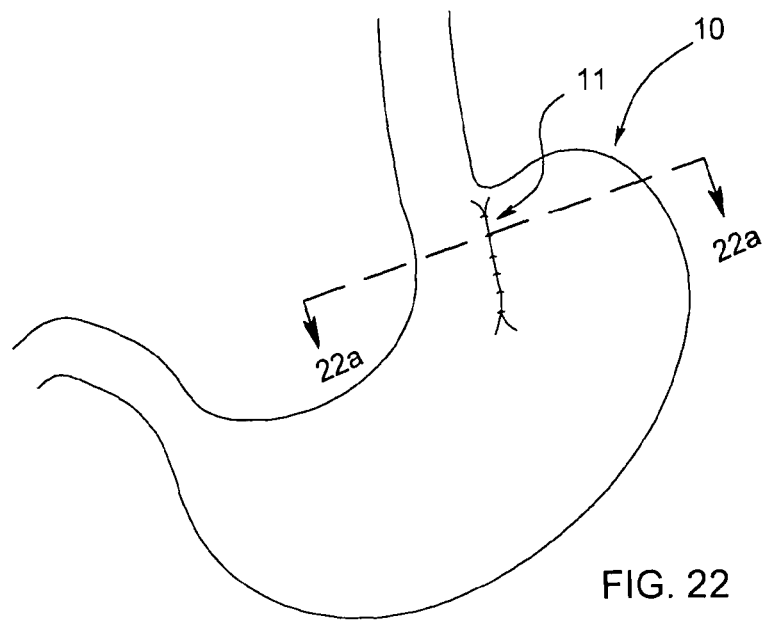
FIG. 22 is an anterior schematic view of a stomach after the procedure demonstrated in FIGS. 13-21 is complete.
Figure 22A:
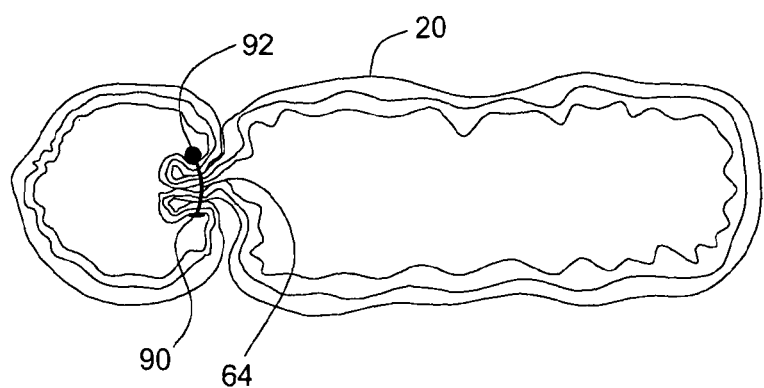

In the manner illustrated in FIGS. 13-21, safe and reliable engagement, approximation and securement of two segments of an organ wall have been demonstrated. FIG. 22 shows the resulting securement line 11, or luminal partition, as seen from the outside of stomach 10. FIG. 22a shows a section of stomach 10 from FIG. 22 taken along line 22a-22a.

The trans-esophageal device 50 and method for forming a gastric pouch 9 provide a number of other advantages. Because the stomach organ 10 is collapsed around substantially the entire exterior surface of the device 50, the configuration of the gastric pouch 9 can be predetermined and controlled by the exterior shape of the device 50. This guarantees a more consistently sized gastric pouch 9, reduces the need for visualization, and allows the minimally-invasive obesity treatment to be performed relatively quickly and without the necessity of substantial amounts of training.

Figure 23:
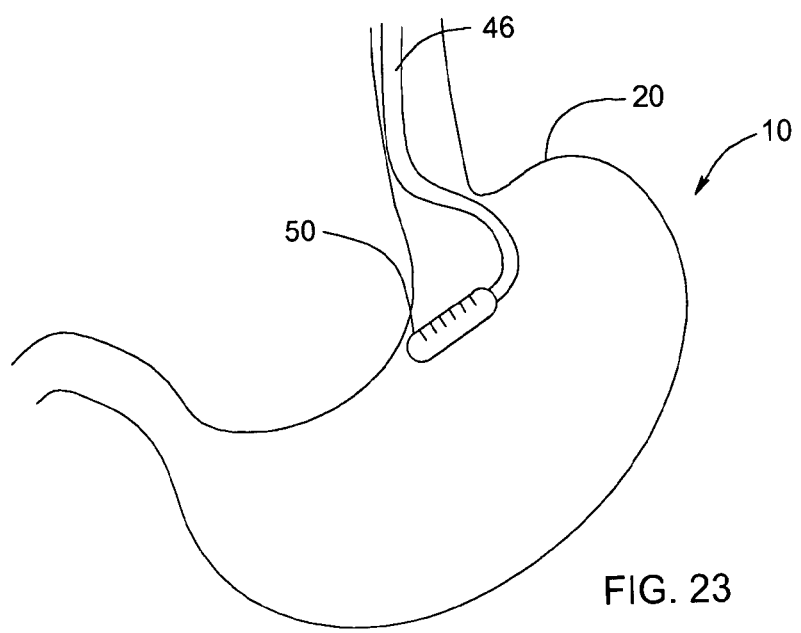
FIG. 23 is a cutaway view of the stomach, showing positioning of the device of FIG. 9 for creating a gastric partition.
Figure 24:
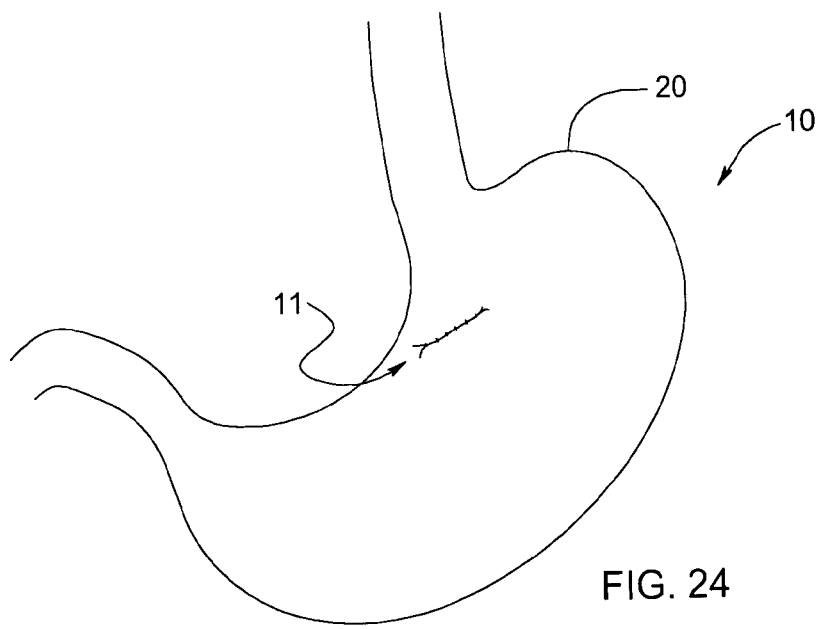
FIG. 24 is a schematic view of the stomach of FIG. 23, showing the resulting position of the gastric partition.

FIGS. 23-26 illustrate a two-step procedure for creating two luminal partitions utilizing device 50. In FIG. 23, device 50 is positioned as shown to create a gastric partition, or securement line 11, in the location shown in FIG. 24. It will be understood that with device 50 positioned toward the center of the lumen of stomach 10, the process of stretching rugae 30 will not be exactly like that shown in FIG. 16, since in FIG. 16 device 50 is positioned with hinge 54 adjacent the lesser curvature 16 of stomach 10 and the length of stomach wall 20 available for stretching closely matches the circumference of device 50. As such, in the case shown in FIG. 23, the stretching process will likely take a few more iterations than in the case shown in FIG. 23. Nonetheless, a durable securement line 11 can be formed as shown in FIG. 24 by following essentially the same steps as in FIGS. 13-21.

Figure 25:
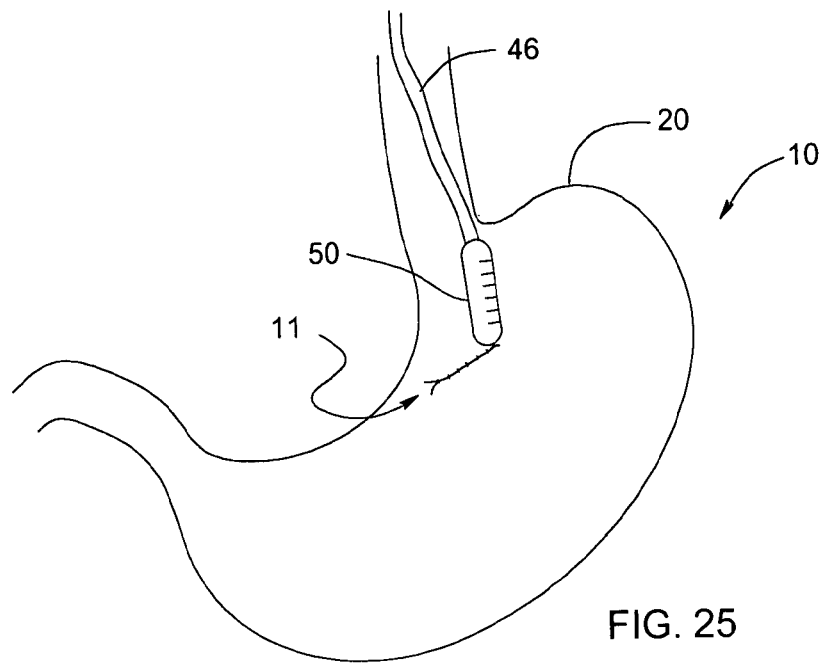
FIG. 25 is a cutaway view of the stomach, showing positioning of the device of FIG. 9 for creating a second gastric partition.

FIG. 25 shows the second step of the two-step process, wherein device 50, after having been reloaded or replaced, is positioned above the securement line 11 formed during the first step, in a location similar to that shown for the procedure of FIGS. 13-21. As such, a second luminal partition can be formed using the steps illustrated in FIGS. 13-21. The resulting sets of two securement lines 11, as seen from outside the stomach 10, are illustrated in FIG. 26.

Figure 26:
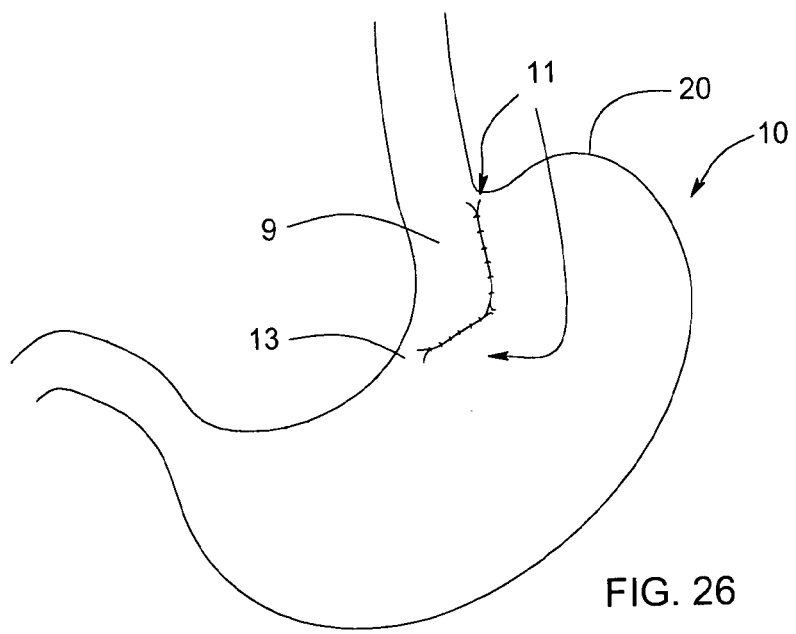
FIG. 26 is a schematic view of the stomach of FIG. 25, showing the resulting position of the second gastric partition, and the resulting pouch formed by the two partitions.

While a single securement line 11 extending from the Angle of His 32 toward into the lumen of the stomach 10 can be useful in the treatment of obesity and GERD, the two-partition arrangement shown in FIG. 26 is preferable, since it creates more of a defined gastric pouch space 9 with a narrow outlet 13 to restrict the outflow of material from gastric pouch 9. As discussed previously, adding a restrictive outlet to a luminal pouch may be desirable in order to delay emptying of the pouch. In a stomach this may sustain the feeling of fullness while restricting further food intake.

Over time, pressure exerted by food against the walls 20 of the gastric pouch 9 will tend to permanently dilate the gastric pouch 9. To minimize such dilation, gastric pouch 9 may be modified by a variety of methods and devices. For example, the muscularis 24 of the walls surrounding gastric pouch 9 may be altered by the application of thermal energy, causing shrinkage of the collagen fibers and an overall tightening of the muscle. Radio frequency (RF) energy may be applied directly to the muscularis 24 using needle electrodes or other electrode arrangements to accomplish such shrinkage and tightening. Alternative ways of imparting thermal energy to the muscularis 24 without damaging the intervening mucosa 28 include, but not by way of limitation, applying microwave energy to the muscularis 24 and direct heating by electrically-heated needle tips that penetrate the muscularis 24. Still another process for modifying the walls of gastric pouch 9 consists of injecting of one or more sclerosing agents into the muscularis 24 using an endoscopic injection needle passed through the working channel of a flexible endoscope, causing scarring and tightening of the muscularis 24. Examples of sclerosing agents that may be used include, but not by way of restriction, detergent agents (e.g., Sodium Morrhuate, Ethanolamine Oleate, Sotradecol, Polidocanol, Scleremo), hypertonic and ionic solutions (e.g., Hypertonic Saline, Sclerodex, Polyiodinated), and cellular toxins.

Additional ways to inhibit dilation of the gastric pouch 9 include modifying the properties of the tissue lining the gastric pouch 9 by, for example, mechanically wounding the tissue (e.g., mucosectomy), surface chemical treatment (alcohols, alkyls, acids, etc.) of the tissue, ablating tissue or causing tissue necrosis using a tissue freezing technique.

Figure 27:
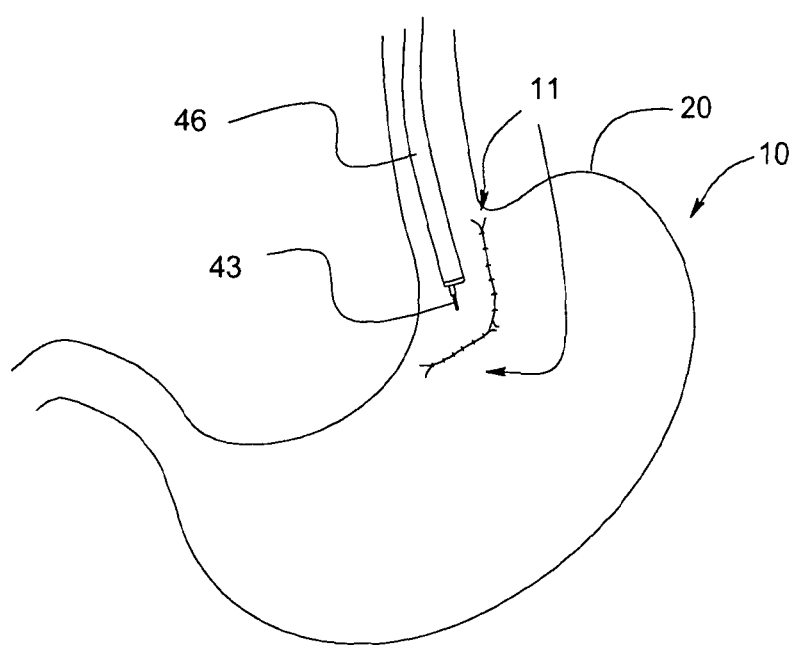
FIG. 27 is a cutaway view of the stomach showing an endoscopic device for modifying the walls of the gastric pouch.

FIG. 27 illustrates a general approach to modifying the properties of the stomach wall 20 surrounding the gastric pouch 9 in order to minimize the amount of dilation of the gastric pouch 9. In the figure, an endoscopic accessory 43 is deployed into the gastric pouch 9 through the working channel of a flexible endoscope 46. The accessory may be, for example, an injection needle, a cauterizing electrode, an argon plasma coagulator, a laser, a mucosectomy snare, an RF electrode, a microwave antenna, or a cryogenic probe.

In a variation of device 50, one or more pledgets may be deployed in conjunction with the activation of the securement function of device 50. With reference to FIGS. 11 and 11a, a pledget 83a may be loaded over each needle 62 on the deployment carriage 80 such that when the sutures 64 are deployed, a pledget 83a will be trapped between the surface of the captured stomach wall 20 and ball anchor 92. Similarly, a pledget could be loaded on the top face of the needle catcher 81 and thereby deploy a pledget or pledgets 83a which get trapped between the bottom face of the captured stomach wall 20 and the T-anchor 90. Using pledgets 83a with the securement devices in securing the stomach walls 20 provides strain relief between the anchoring elements 90, 92 and the surface of the tissue, thereby providing more durable tissue securement and preventing the securement line 11 from separating and the gastric pouch 9 from failing over time. Example pledget strips that may be used are sold under the name Peri-Strips Dry® sold by Synovis Surgical Innovations of St. Paul, Minn. Peri-Strips Dry® is composed of two strips of biological tissue derived from bovine pericardium. However, other types of pledgets and other types of pledget material may be used, for example, but not by way of limitation, Teflon (ePTFE) pledgets may be used. Pledgets 83a may be made from any material available to those skilled in the art that is suitable for use in preventing the suture anchors 90, 92 from abrading the tissue of the stomach wall 20. For example, resilient pledgets may also be used, such as a thin strip of silicone or thermoplastic elastomer (TPE) reinforced with stretchable webbing such as nylon to provide tear resistance.

Figure 28:
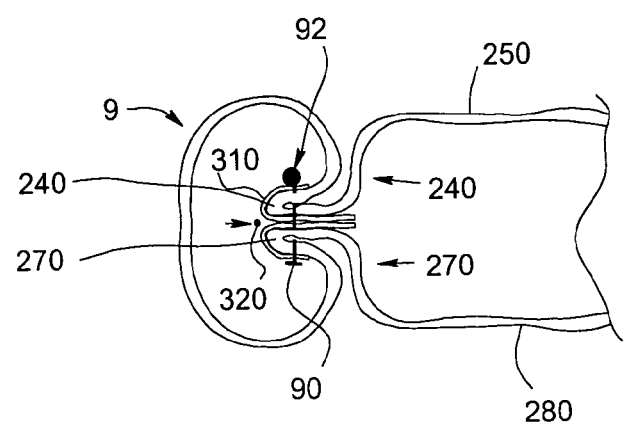
FIG. 28 is a cutaway view of a stomach that has been modified per the procedure shown in FIGS. 13-21, with the addition of reinforcing material.

It may be desirable to cause wall-to-wall tissue adhesion or ingrowths to create a more durable securement line 11. To facilitate this, at least one segment of biocompatible material 310 may be disposed between the layers of approximated tissue 240, 270. FIG. 28 shows a cutaway view of a stomach that has been modified per the procedure illustrated in FIGS. 13-21, with the addition of a biocompatible material 310 extending between the approximated layers 240, 270 of stomach wall 20. In the embodiment shown, the one or more segments of material 310 have been deployed not only to promote wall-to-wall tissue adhesion or in-growth between the layers, but also to act as strain-relieving pledgets and thereby inhibit pull-through of the tissue securement devices 90, 92.

To promote wall-to-wall tissue adhesion or in-growth, the material 310 is preferably porous enough to allow tissue in-growth, or may be formed with holes or an open lattice structure to allow tissue to grow through the material. An exemplary material that may be used for this purpose is a polypropylene mesh, such as Marlex® mesh (CR Bard, Cranston, R.I.).

While it may be desirable from a durability standpoint to promote tissue in-growth between the approximated layers of stomach wall 20, this presents a difficulty in reversing the procedure, since cutting through the ingrown tissue seam may present the risk of perforation of the stomach wall 20. As such, a further advantage of the embodiment illustrated in FIG. 28 is that the two-layers of material 320 shown may be used as a guide in cutting through the in-grown segment of tissue without risk of perforation. To cut through the in-grown tissue, a separation mechanism 320, which may be a thin, high-strength cutting wire, can be moved in the direction of the arrow shown in FIG. 28 to separate the one or more layers of material 310. The cutting wire may be energized with cauterizing energy (radio frequency) to facilitate the cutting process and to provide coagulation of small vessels encountered during the cutting process. In an alternative embodiment, the element 320 may be embedded or integrated into the one or more segments of material 310 to make it easier to perform the separation. Prior to pledget separation or cutting with the pledget separation mechanism 320, tissue securement devices 90, 92 may be cut.

Figure 29:
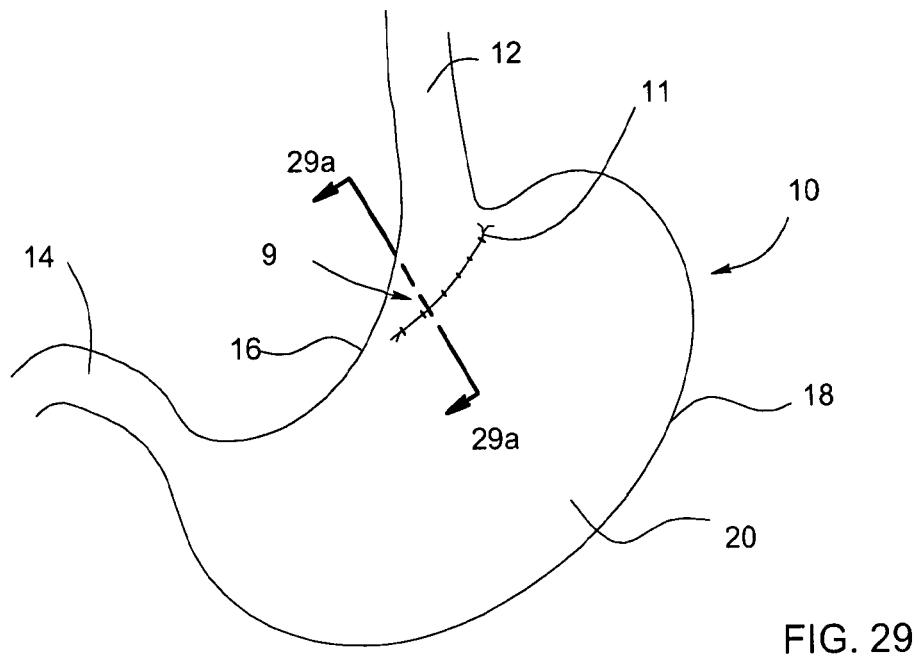
FIG. 29 is an anterior schematic view of a stomach, showing the position of a gastric partition created by attachment of a section of biocompatible material.
Figure 29A:
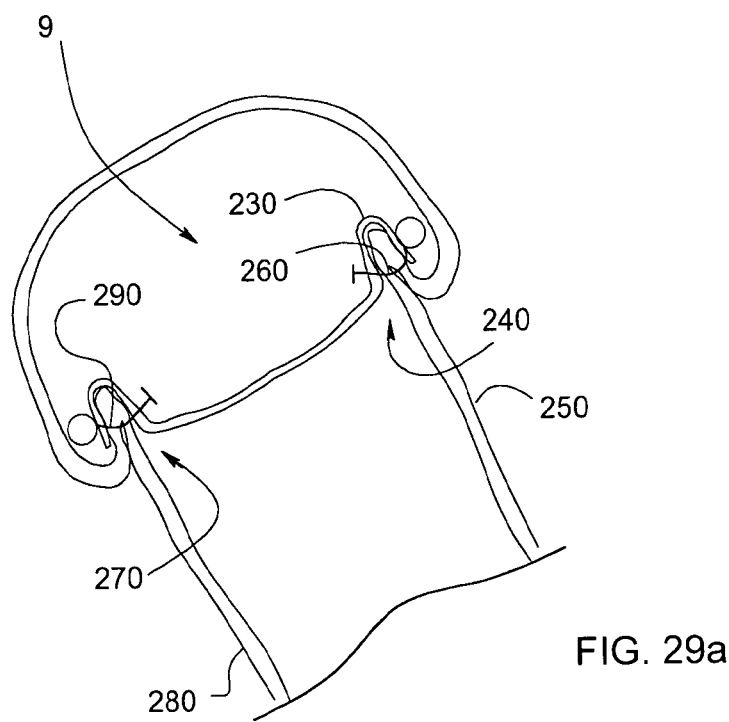
FIG. 29a is a section view taken along line 29a-29a in FIG. 29 showing the securement of the biocompatible material between the anterior and posterior walls of the stomach.

With reference to FIGS. 29 and 29a, a gastric pouch 9 constructed in accordance with an alternative embodiment of the invention will be described. Instead of stomach walls 20 being directly secured to each other along a securement line 11 to form the gastric pouch 9 discussed above, the gastric pouch 9 may be formed by providing one or more strips or pieces of material to form a partition 230 between walls 20 being secured together.

In the embodiment of the gastric pouch 9 shown in FIG. 29b, the partition 230 is secured to an invaginated tissue fold 240 of a first wall 250 through one or more tissue securement devices 260 and is secured to an invaginated tissue fold 270 of a second wall 280 through one or more tissue securement devices 290. In this embodiment, opposite walls 250, 280 are separated or spaced from each other and partition 230 thereby defines a portion of the gastric pouch 9. The partition 230 also mitigates the possibility of the tissue of the stomach walls 250, 280 adhering to one another after a period of time, making the procedure more easily reversible (by just cutting through the material, for example).

The partition 230 may be made from a variety of materials such as, but not limited to, biological tissue, bovine pericardium, and Teflon (ePTFE). Alternatively, partition 230 may be made from a resilient elastic material that stretches if large volumes of food are forced into the gastric pouch 9. In such an embodiment, the partition 230 creates a "shock absorber" effect that helps reduce tension on the tissue securement devices 260, 290, inhibiting the tissue securement devices 260, 290 from pulling out of the tissue over time.

FIGS. 30-37 illustrate various embodiments of a transesophageal suturing device 140 to safely and reliably administer endoluminal therapy. The suturing device 140 illustrated in FIG. 30 is shown attached to the end of a flexible endoscope 46 by way of fastening ring 158. Endoscope 46 is shown having an imaging lens 154, an air/water nozzle 155, illumination lenses 156, and a working channel 157. In alternative embodiments, one or more of the imaging lens 154, the air/water nozzle 155, illumination lenses 156, and the working channel 157 may not be present or may be incorporated into the device 140. A throat 159 having a flexible section 161 and a device housing 150 extend distally from the ring 158. The housing 150 of the suturing device 140 generally has a substantially flat face 160, and a curved back 162, and also includes a needle entry hole 164 and needle exit hole 166 through which a semicircular needle 142 may pass. A slot 146 may be provided in the housing to allow a suture thread 143 attached to the needle 142 to pass between a needle path and the exterior of the device 140 as the needle is cycled repeatedly through its substantially circular path. With reference to FIGS. 31 and 31a, the tool 140 generally includes a semicircular needle 142 advanced by a needle driving mechanism 144. Needle 142 is driven by a swing arm 168 with a latching mechanism 170 configured to engage a plurality of notches 172 formed in the needle 142.

A typical stitch cycle will now be described with reference to FIGS. 31-34. The suturing device 140 may be inserted into the stomach 10 of a patient with the needle 142 in the position shown in FIG. 33. In this position, the sharp ends of the needle 142 are held inside the device housing 150, thus preventing damage to the esophagus 12 or stomach 10 during insertion of the device 140. Providing the needle 142 in this position also allows a clinician to visually align the needle 142 with a marked location for a suture stitch.

As shown in FIG. 33, the swing arm 168 is in a first position in preparation for moving the needle 142. In order to move the needle 142, a clinician pulls on the pull wire 178 (see FIG. 35) causing the swing arm 168 to pivot about its axis 169 to the second swing arm position shown in FIG. 34. The latching mechanism 170 engaged with the first notch 172a will cause the needle 142 to be moved along with the swing arm 168 to the position of FIG. 34. As the pull wire 178 is released, the swing arm 168 will be returned to its first position shown in FIG. 31. The lock pin 182 engaged with the fourth notch 172d will prevent the needle 142 from being moved backwards by the swing arm 168.

Figure 32:
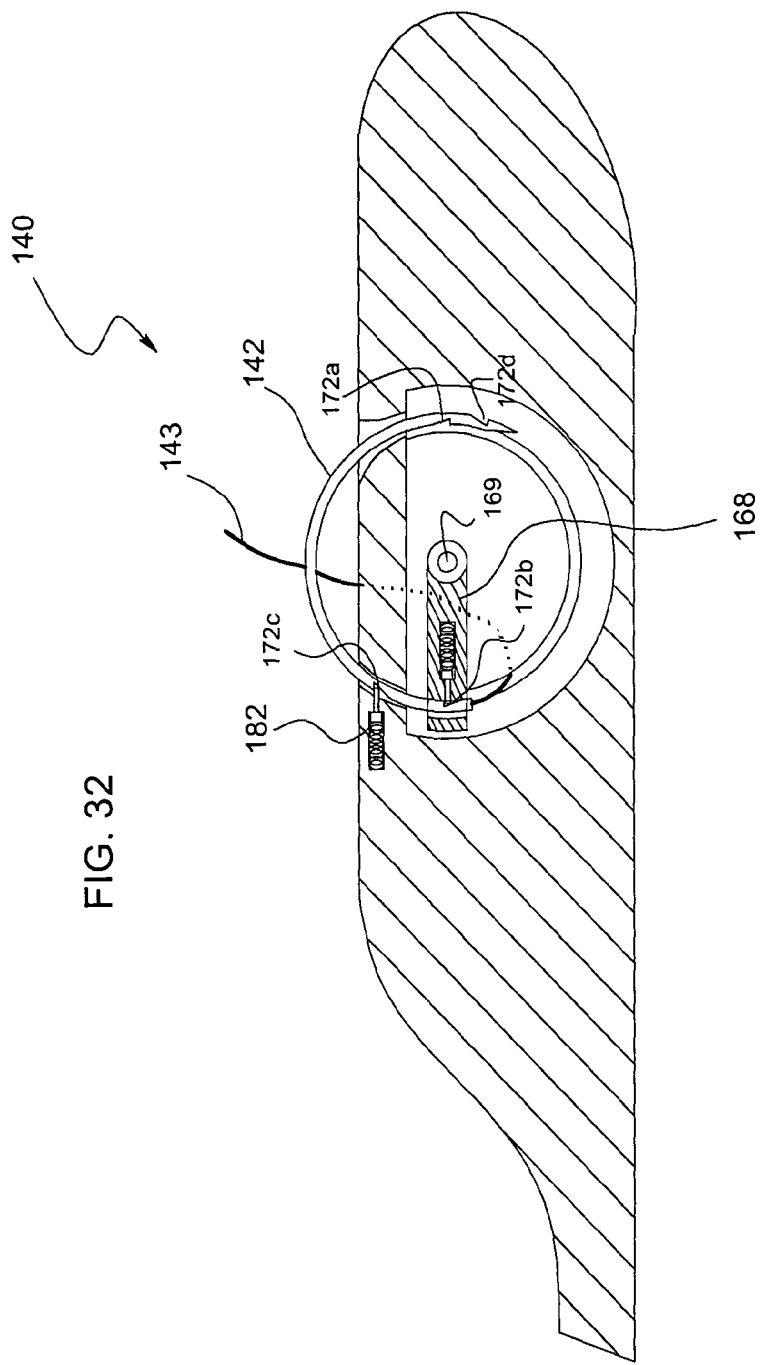
FIG. 32 is a section view of the suture deployment device of FIG. 30, showing the needle deployed.

Once a clinician is prepared to make a stitch, the pull wire 178 may be pulled again, thus causing the swing arm 168 to move to its second position while driving the needle 142 to the position shown in FIG. 32. From the position shown in FIG. 32, the swing arm 168 may again be returned to its first position as shown in FIG. 33. The above steps may be repeated as necessary to drive a plurality of stitches through a stomach wall 20 or other tissue. As will be clear to those skilled in the art in view of the present disclosure, the suture thread 143 will continue to extend through the slot 146 and out of the device housing 150 throughout the stitching process.

With reference to FIGS. 31 and 31a, the needle 142 of the embodiment shown generally includes first notch 172a, second notch 172b, third notch 172c, and fourth notch 172d. The first notch 172a and second notch 172b are formed on an internal side 181 of the curvature spaced such that they will be engaged by the swing arm 168 to drive the needle 142 through its circular path. The third notch 172c and fourth notch 172d are positioned on portions of the needle 142 on an outside 183 of the curvature. The third notch 172c and fourth notch 172d will typically be engaged by the spring-biased lock pin 182 in order to retain the needle 142 in the positions shown in FIGS. 33 and 31 respectively as the swing arm 168 is moved between its first position (shown in FIGS. 33 and 31) and its second position (shown in FIGS. 34 and 32) in order to continue advancing the needle 142.

Figure 35:
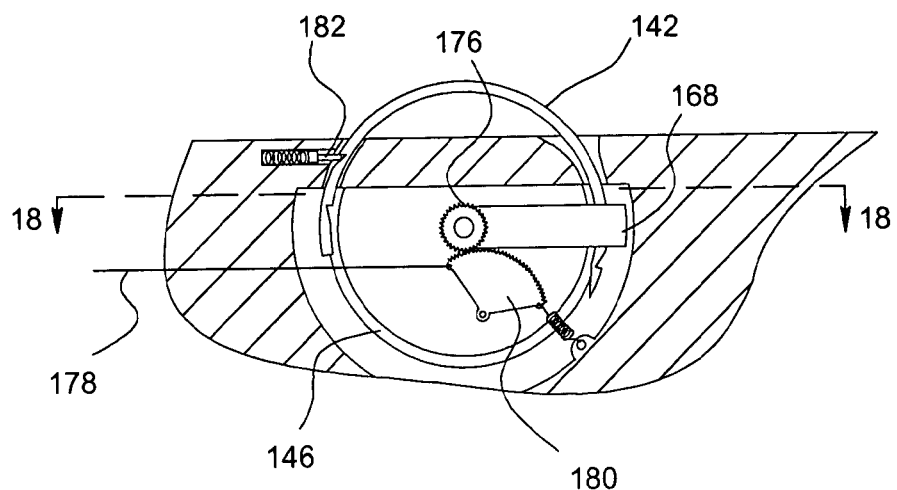
FIG. 35 is a side section view showing actuating mechanisms useful in a suture deployment device.
Figure 36:
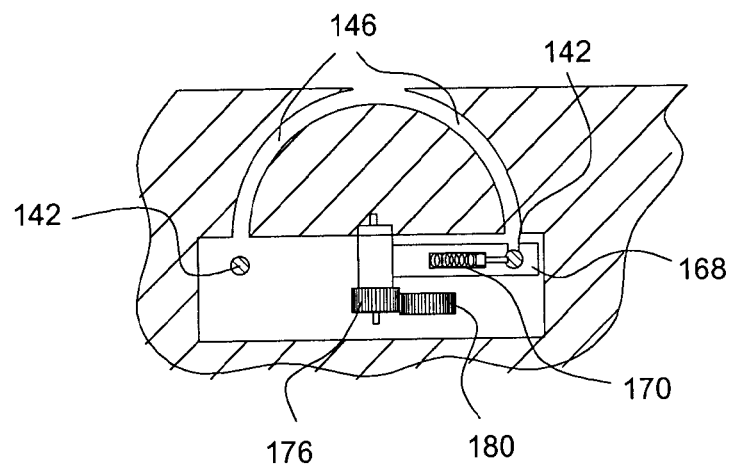
FIG. 36 is a top section view of the actuating mechanisms of FIG. 17 taken through line 18-18.

As shown in the cut-away view of FIG. 35, the swing arm 168 is typically mounted to a pinion spur gear 176 such that the swing arm 168 will rotate with the spur gear 176. A pull wire 178 may be attached to a rocker gear 180 which may be used to actuate the spur gear 176 in order to move the swing arm 168. The gear ratio between the rocker gear 180 and the spur gear 176 is generally at least 2:1 in order to allow the swing arm 168 to pivot through a full 180 degrees. In other embodiments, larger or smaller gear ratios may be used, resulting in increased or decreased pivoting range. The rocker gear 180 may be provided with teeth along more than 90 degrees in order to allow additional motion of the swing arm 168. The rocker gear 180 may be biased toward a first position by a spring or other biasing mechanism, or the rocker gear 180 may be provided with a second pull wire to allow the rocker and thereby the swing arm 168 to return to a first position (as shown in FIG. 35). Alternatively, the needle 142 may be driven by one or more rollers, ratchet gears, or any other appropriate mechanism recognized as suitable for driving the needle 142 about its circular path as shown and described herein.

Needle 142 is typically made of stainless steel; however it may be made from any material suitable for use in surgical needles. The notches 172 may be formed by any appropriate method. The radius of curvature, and thus the semi-circumferential length of the needle will typically be chosen to allow the needle 142 to pierce the outermost wall layer, the serosa layer 22 of the stomach 10 under assumptions of maximum wall thickness. The arc height 184 is indicated in FIG. 33 as the distance between the suture tool face 160 and the inner surface 181 of the needle (in the deployed position as shown). Of course, the thickness of stomach walls 20 in humans tends to vary, however, studies indicate that a stomach wall thickness of up to about 0.20 inches may be expected, and in one embodiment an arc height of up to about 0.22 may be used.

A suturing device such as that shown in FIGS. 30-37 could also be configured to drive two or more needles 142 spaced side-by-side or end-to-end. The particular orientations of the two or more needles 142 may be chosen to suit the particular suture pattern desired.

Figure 37:
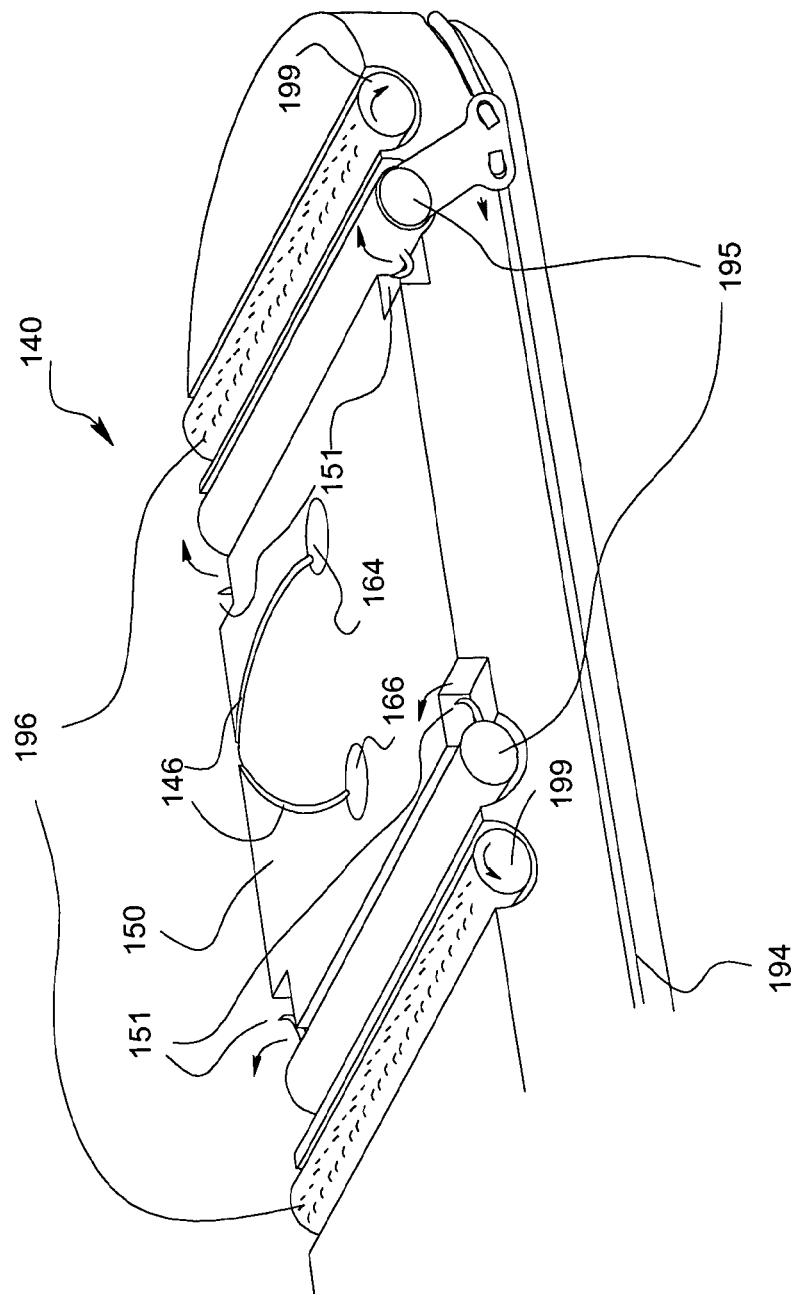
FIG. 37 is a perspective view of a different suture deployment device having mucosal stretching and muscularis engagement mechanisms.

The suturing device 140 may also be provided with mechanisms to manipulate the mucosa 28, as is shown in the device 140 of FIG. 37, which includes rollers 196 configured to spread and flatten the mucosa 28 in the area between the rollers 196 in opposite directions 199. Once the mucosa has been sufficiently stretched and flattened by the rollers, the hook needles 151 may be rotated away from one another to selectively engage the muscularis 24 of stomach wall 20 and hold the wall securely while a stitch is placed. Such engagement of the muscularis 24 also allows device 140 to pull stomach wall 20 into the lumen of the stomach 10, creating a safety gap between the outer wall of the stomach and surrounding structures, as was described previously. In the embodiment of the device 140 shown in FIG. 37, hook needles 151 may be actuated by any appropriate mechanism such as, by way of example only, a pull wire 194 configured to pivot an axle 195 to which the needles 151 may be attached.

Figure 38:
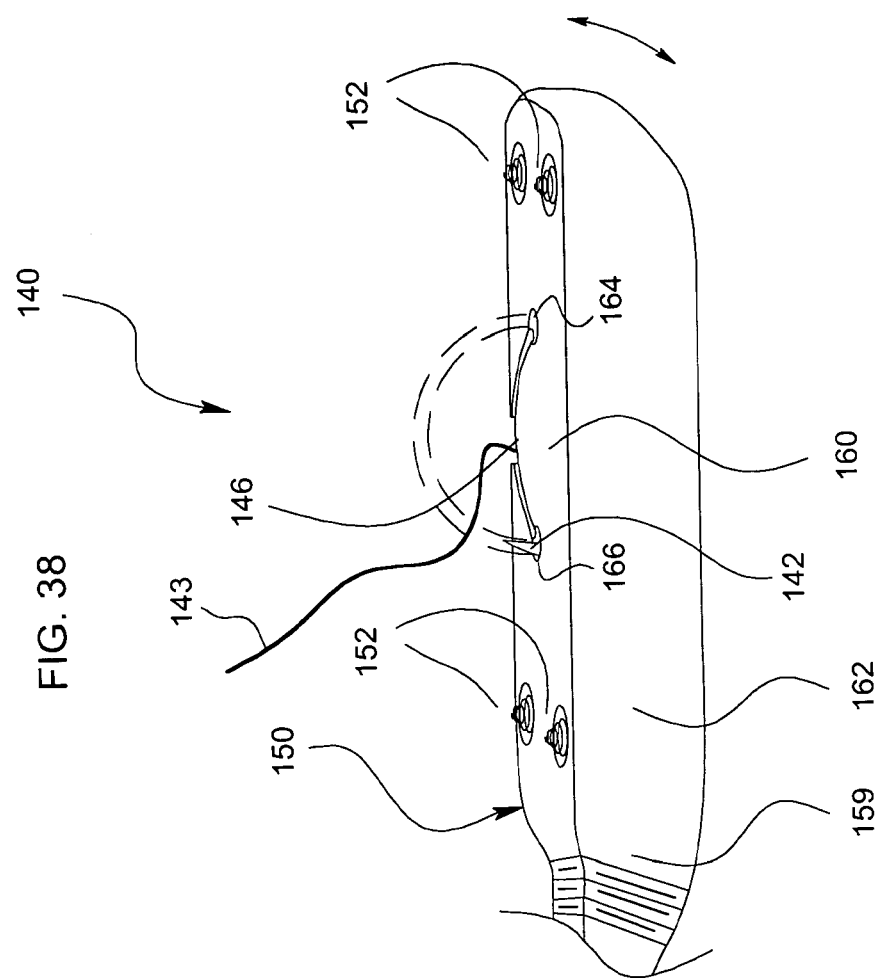
FIG. 38 is a perspective view of the suture deployment device of FIG. 30 having tissue engagement mechanisms.
Figure 39:
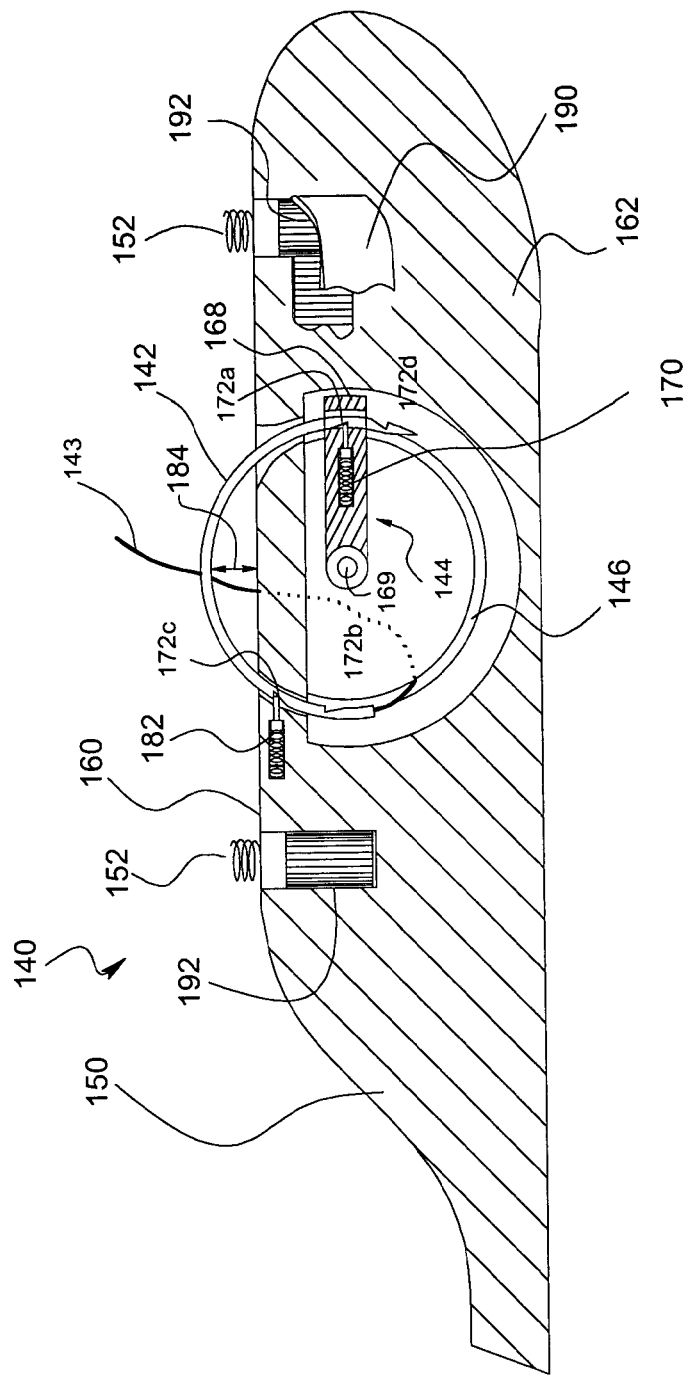
FIG. 39 is a side section view of the suture deployment device of FIG. 38.

In an alternative embodiment of suturing device 140 illustrated in FIGS. 38 and 39, corkscrew needles 152 are shown for temporarily securing or anchoring the device 140 to the stomach wall 20. In a preferred method of use of this embodiment, the mucosa 28 is first smoothed or flattened by either moving the arc of curved needle 142 across the mucosa 28, or insufflating the lumen of the stomach 10 to the point where the mucosa 28 and any rugae 30 are stretched out. Once the mucosa 28 is substantially flat, the corkscrew needles 152 can be deployed to engage the muscularis 24. In the embodiment shown, corkscrew needles 152 are configured to be rotated and thereby drawn into the tissue of the stomach wall 20 a sufficient depth that they engage the muscularis 24 of the stomach wall 20. Alternatively, the securing elements may comprise hook-shaped needles 151 (as shown in FIG. 37), barbed needles, suction nozzles, or other devices sized and configured to at least temporarily engage a portion of the stomach wall typically including at least a portion of the muscularis 24. The securing elements may be actuated by one or more push/pull wires attached to a belt, chain, cable etc. The belt, chain, or cable is generally configured to rotate the securing elements a desired amount in order to engage the stomach wall. For example, in the illustrated embodiment of FIG. 39, the securing elements 152 are rotated by a toothed belt 190 which engages spur gears 192 mounted to the securing elements 152. It will be appreciated that any appropriate mechanism may alternatively be used to achieve the desired temporary securing of the device to the stomach wall 20. The securing elements are preferably sized such that they will not exit the serosa 22 of the stomach 20, thus protecting the adjacent organs. In some embodiments, a penetration depth of about 0.06" to about 0.10" may be suitable, and in one embodiment, a depth of about 0.08" is used. The securing elements are typically spaced relative to the needle entry and exit holes 164, 166 such that the stomach wall tissue will be tightly held in the area to be sutured in order to allow the semicircular needle 142 to penetrate to its desired depth through the stomach wall 20.

Figure 33A:
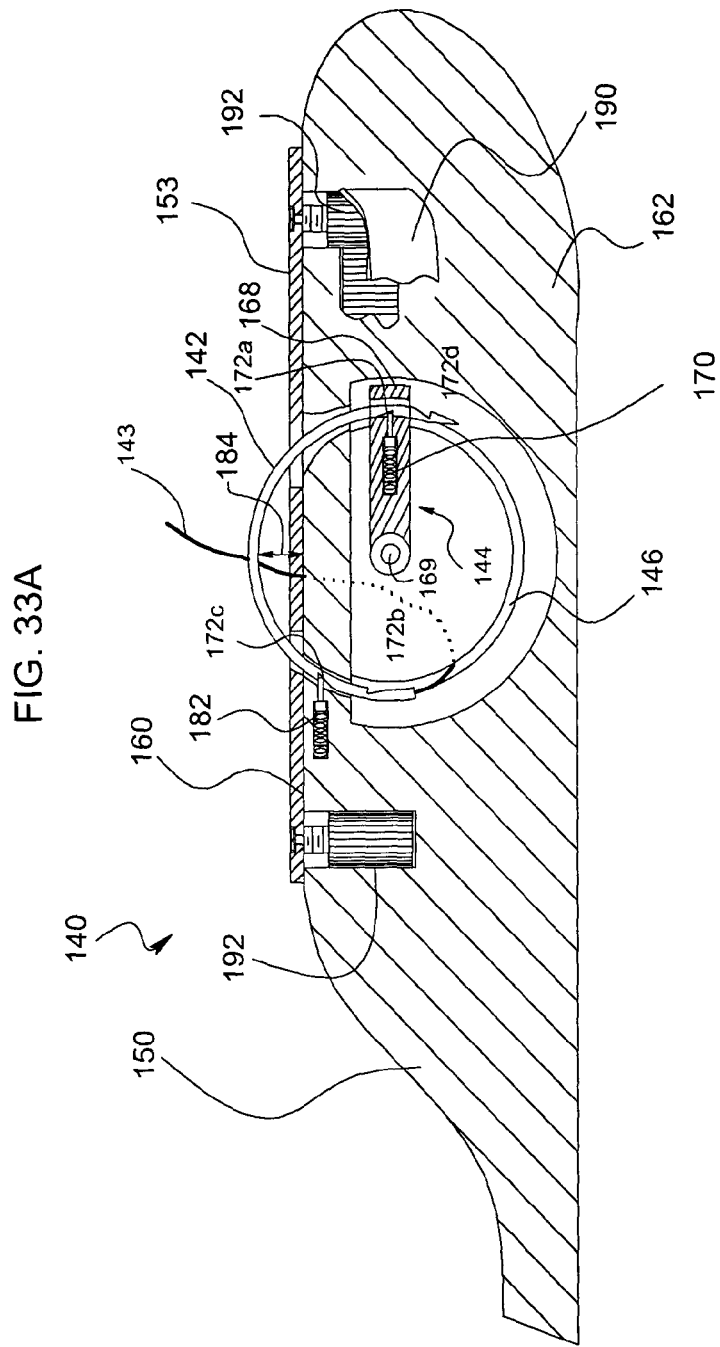
FIG. 33a is a section view of a variant of the suture deployment device of FIG. 30, showing an adjustable horizontal surface on the face of the device to control the depth of needle deployment.
Figure 34:
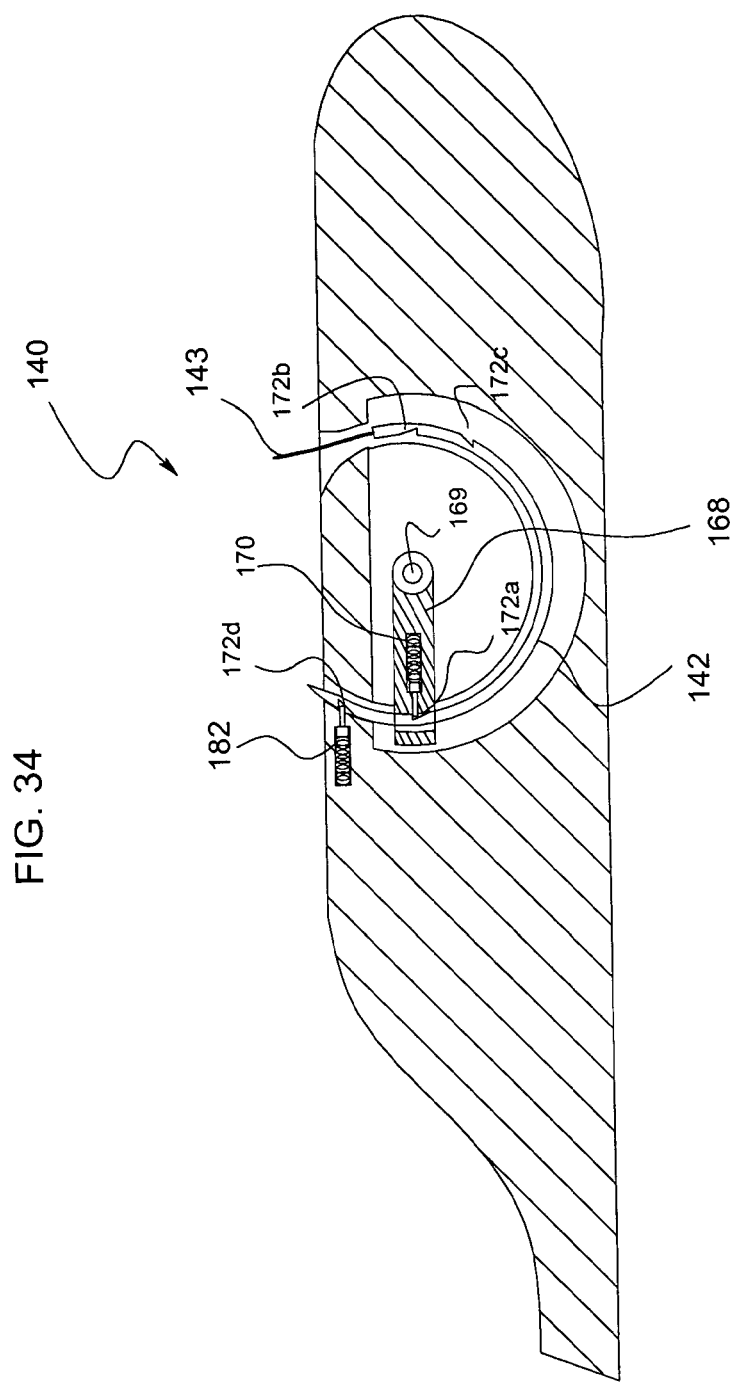
FIG. 34 is a section view of the suture deployment device of FIG. 30, showing the needle retracted.

FIG. 33a shows a variant of suturing device 140 incorporating an adjustable shim 153 on the face of housing 150. Assuming the device 140 is kept in close contact with the mucosa 28, as by the securement elements discussed above, adjustment of shim 153 down or up will increase or decrease, respectively, the depth of penetration of needle 142. Adjustment of shim 153 may be done using a mechanism comprising a toothed belt 190 which rotates a series of screw elements that raise or lower the surface of shim 153.

In another aspect of the present invention, it may be desirable to measure the electrical impedance of the tissue in the vicinity of a tissue-penetrating element. As discussed previously, such impedance data can provide information about the depth of penetration, can provide confirmation that the element has or has not penetrated the wall, and can provide a warning that the element may have encountered an unwanted structure such as a blood vessel.

Impedance sensing may be done using DC current or voltage but is more reliable when an AC current or voltage is passed between the electrodes (because of the electrolytic nature of biological fluids). Current-based measurement is generally preferred because it fixes the amount of current regardless of how low the impedance gets. (In contrast, voltage-based impedance measurements can allow the current to increase to levels that can cause tissue damage.) With an AC current impedance measurement circuit, the induced voltage is measured and then the impedance is calculated. For low frequencies, the impedance is roughly equal to the ratio of the voltage over the current. Higher frequencies can be used for more precisely discriminating between specific tissue types by measuring the complex impedance of the tissue. These complex components include both the capacitive and resistive factors, rather than only the resistive components that the low frequency or DC measurements determine.

Figure 40:
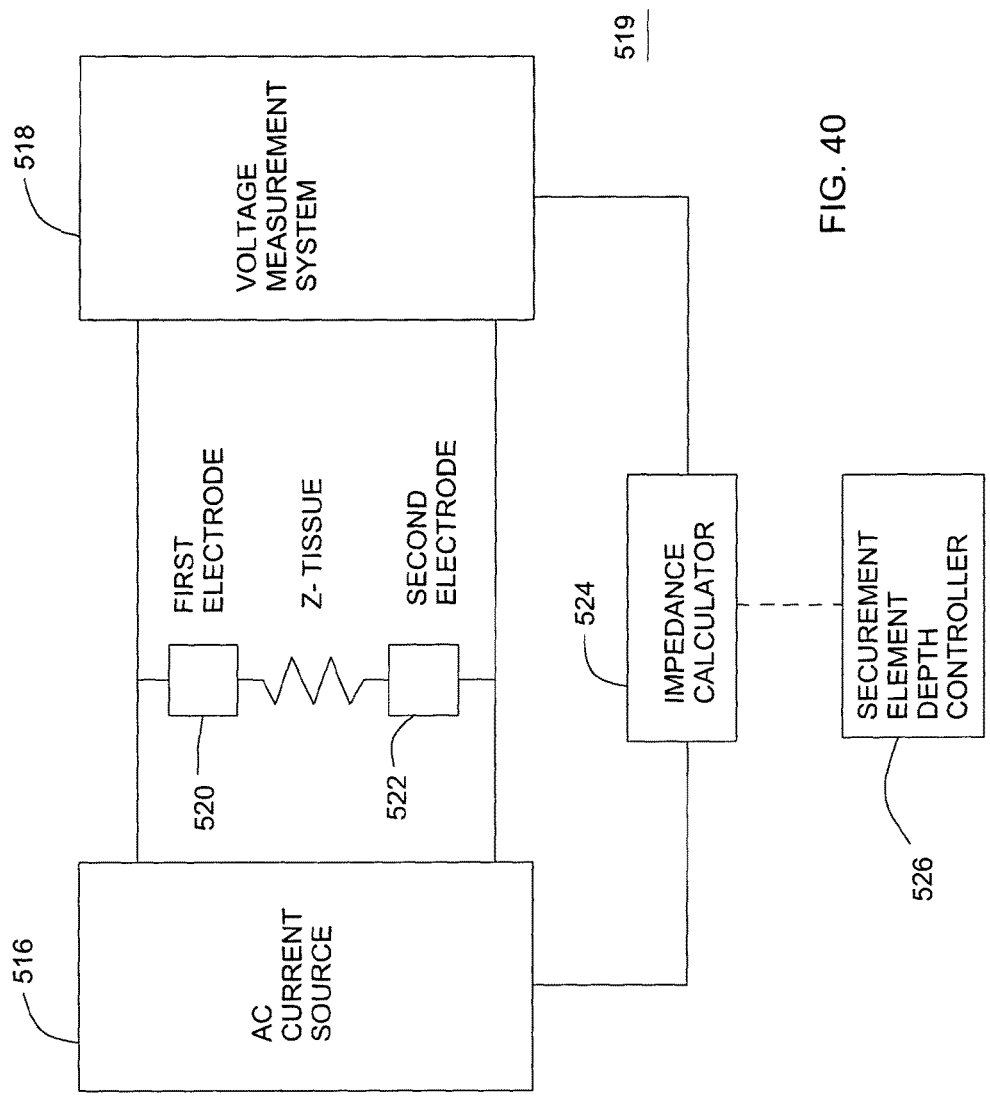
FIG. 40 is a block diagram of a tissue impedance measurement system.

FIG. 40 shows a basic impedance measurement system 519, consisting of an AC current source 516, a voltage measurement system 518, a first electrode 520, a second electrode 522, an impedance calculator 524, and an optional controller to automatically adjust the depth of penetration of a securement element, such as a needle.

Impedance may be measured using either a monopolar or a bipolar approach. FIG. 41 illustrates a monopolar embodiment of the suturing device 140 discussed above. In this illustration, the tip of needle 142 functions as the first electrode 520, and an area on the surface of device 140 serves as the second electrode. The needle swing arm 168 makes electrical contact with the needle 142, and the swing arm 168 in turn is connected to a wire leading to an external impedance measurement system 519. In this embodiment, the tissue impedance is measured between the tip of the needle and the electrode on the surface of device 140.

Figure 42:
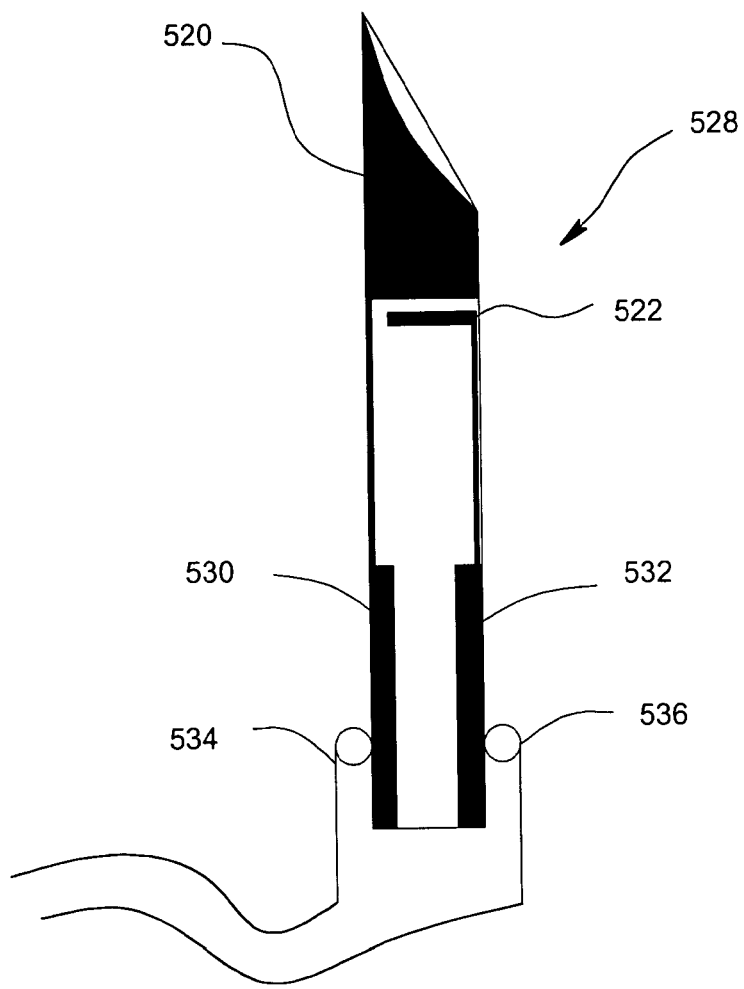
FIG. 42 is a perspective view of a hollow needle adapted to measure tissue impedance.

In a bipolar approach, the impedance is measured between two isolated electrodes in close proximity. As such, it tends to give a more accurate indication of impedance within a specific area. FIG. 42 presents an embodiment of a hollow needle 528 having two electrode areas 520, 522. Two corresponding electrode contact regions 530, 532 make electrical contact with sliding contacts 534, 536, which in turn connect to an external impedance measurement system 519 through a pair of wires.

Figure 40A:
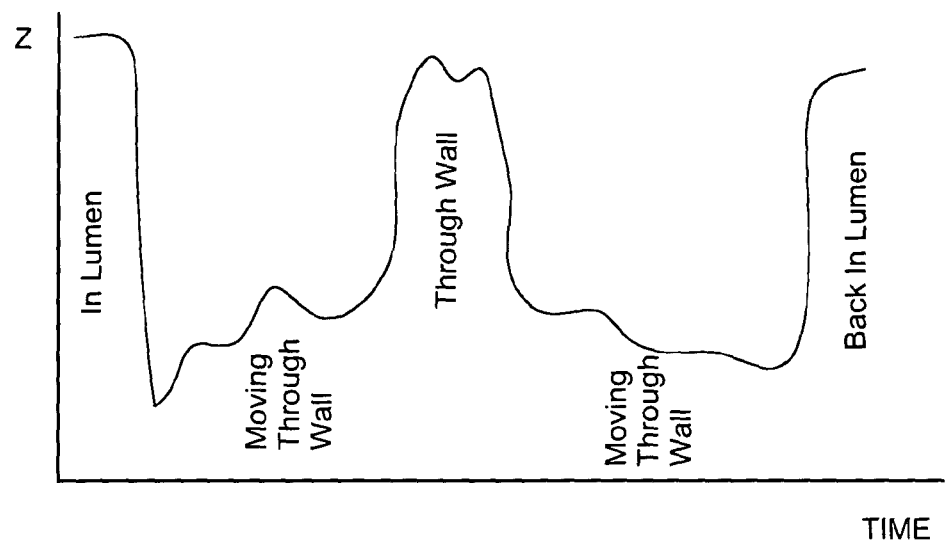
FIGS. 40a and 40b show graphs of tissue impedance at various locations in and around the wall of a hollow organ.
Figure 40B:
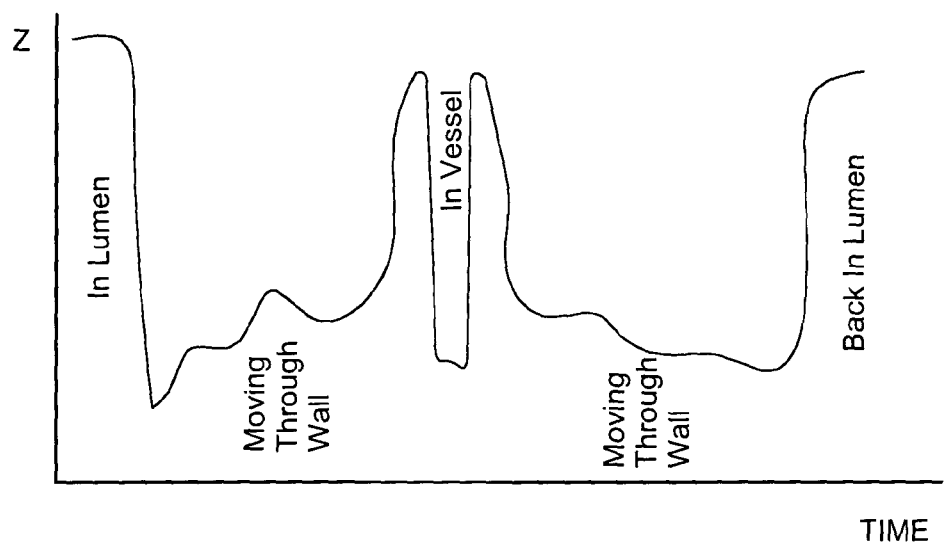

FIGS. 40a and 40b show exemplary graphs of impedance as the needle electrode 142, 520 (shown in FIG. 41) is moved through the stomach wall. Initially, the impedance is infinite until the needle contacts the mucosa 28, whereupon the impedance drops considerably. As it moves further into the muscularis 24, the impedance increase slightly, as the distance between the first and second electrodes increase. When the needle penetrates the serosa 22, the impedance again jumps to a very high level, as shown in FIG. 40a, unless the needle encounters a blood vessel, which is highly conductive, as is depicted in FIG. 40b.

Figure 43:
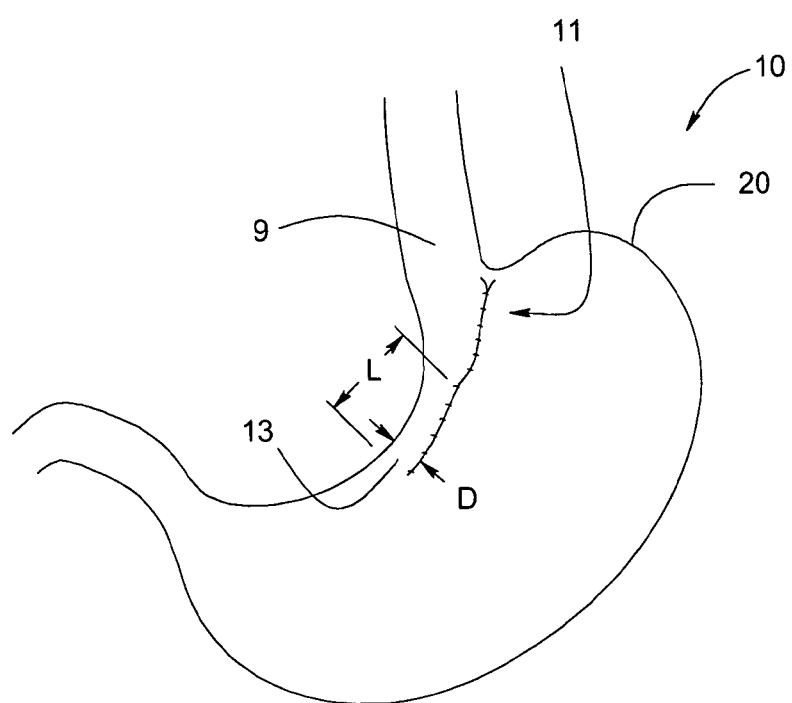
FIG. 43 is an anterior schematic view of a stomach which has undergone a gastric restriction procedure including an elongated restrictive outlet having a length L and diameter D.

FIG. 43 illustrates an application of the stitching device 140 described above. The stomach 10 is shown with a securement line 11 extending from the Angle of His 32 to more than halfway down the lesser curvature 16, forming a gastric pouch 9 that blends into an elongated tubular passage that serves as a restrictive outlet 13 having a diameter D and length L. Such a procedure can be accomplished with the stitching device 140 by placing a first stitch at the distal end of securement line 11, anchoring the suture with an anchoring device such as a knot or a crimpable anchoring element known to those skilled in the art, and then placing sequential stitches proximally until the securement line 11 is complete. It will be appreciated that the suture lines cannot be fully tightened until all of the stitches are placed, otherwise, the lumen would collapse and make it difficult to use device 140. Thus, after the last stitch is placed, a process of sequential tightening of the sutures, starting at the distal end and working proximally, can be employed. Once tightened, the proximal end of the suture can be anchored.

The restrictive outlet 13 formed by the procedure depicted in FIG. 43 has unique properties. First, because it is bordered by the lesser curvature 16, it is less likely to dilate over time than if it were formed elsewhere in the stomach 10. Second, because of its length, it is likely that any such dilation that does take place will occur only at the proximal end of the passage, where the pressure of food being forced into the passage is the highest. By the time the food makes it through the passage, the radial forces exerted on the passage will be minimal, so the distal portion of the passage will remain relatively stable.

Another important facet of the restrictive outlet 13 shown in FIG. 43 is that the restrictive effect can be modified by changing the length or diameter of the passage. Specifically, by lengthening the passage or narrowing the diameter by adding pleats along a wall of the passage (using endoluminal tools similar to those described previously), the restrictive effect increases. In contrast, by shortening the passage or increasing the diameter, the restrictive effect is lessened. As such, this form of restrictive outlet 13 may be used as an adjustable restrictive outlet 13 the effect of which can be modified over time by simple endoscopic adjustments (such as adding or cutting stitches).

Figure 44:
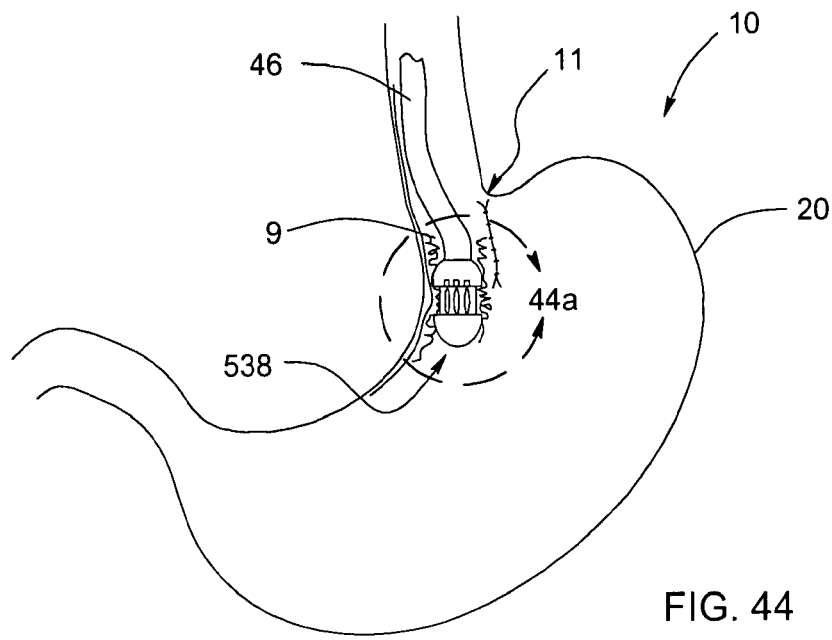
FIG. 44 is a cutaway view of a stomach which has undergone the gastric partition procedure shown in FIG. 22, with an endoscopic device shown for the creation of a restrictive outlet via mucosal bunching.
Figure 44A:
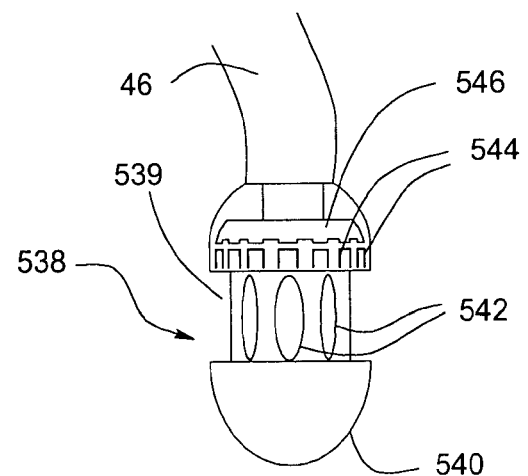
FIG. 44a is an enlarged schematic view of the mucosal bunching device shown in FIG. 44.
Figure 45A:
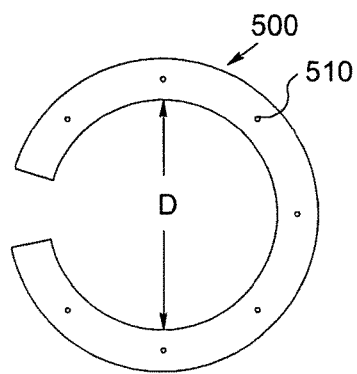
FIGS. 45a-j are schematics views of various devices to reinforce and augment a restrictive outlet to a gastric pouch.
Figure 45B:
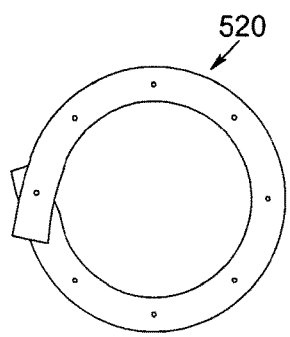
Figure 45C:
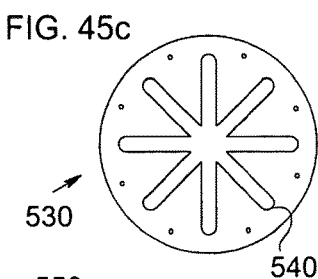
Figure 45D:
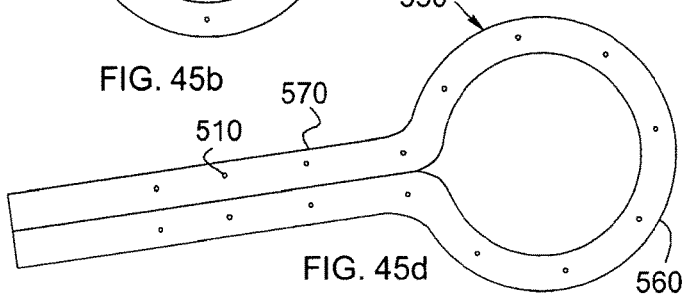
Figure 45E:
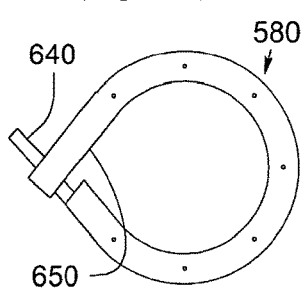
Figure 45G:
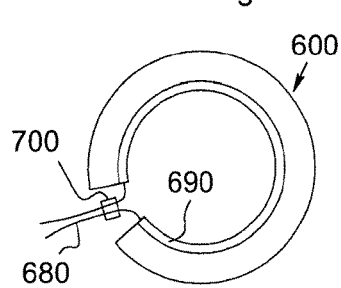
Figure 45I:
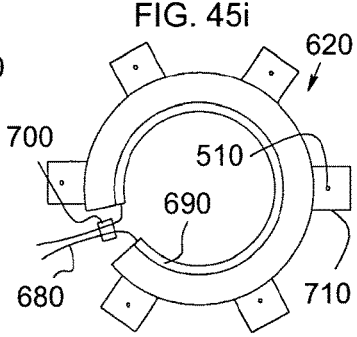
Figure 45F:
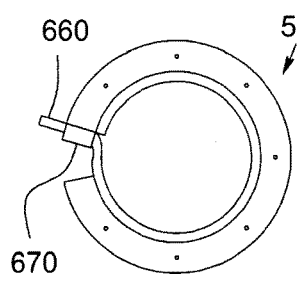
Figure 45H:
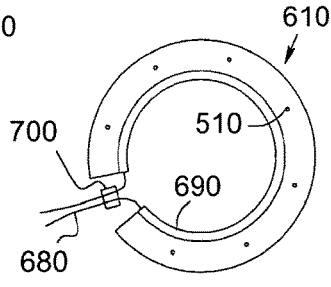
Figure 45J:
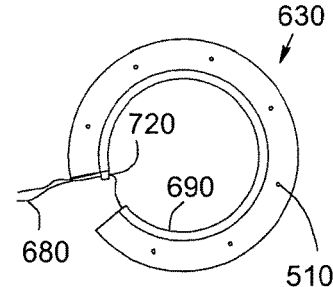

FIG. 44 illustrates another technique for creating a restrictive outlet 13 to a gastric pouch 9. A mucosal bunching device 538 which is generally egg shaped, has a distal anvil 540, an interior space 539 into which mucosa 28 is sucked using suction applied through vacuum ports 542, a radial array of staples 544 and a staple pusher 546. By deploying device 538 into the outlet of a gastric pouch 9 and applying suction through ports 542, mucosa 28 is sucked into the stapling space, and the staples are then pushed through the mucosa and formed against the anvil. In doing so, the mucosa acts a natural flow restrictor to the flow of food out of gastric pouch 9.

To make the technique shown in FIG. 44 more robust, a generally circular shaped pledget may be deployed by the bunching device 538 during the stapling procedure. Many variations of such circular pledgets are shown in FIGS. 45a-j. In certain embodiments, such as those shown in FIGS. 45g-j, and adjustment thread 680 is incorporated, allowing the restrictive outlet to be cinched up or loosened by the clinician endoscopically.

Figure 46:
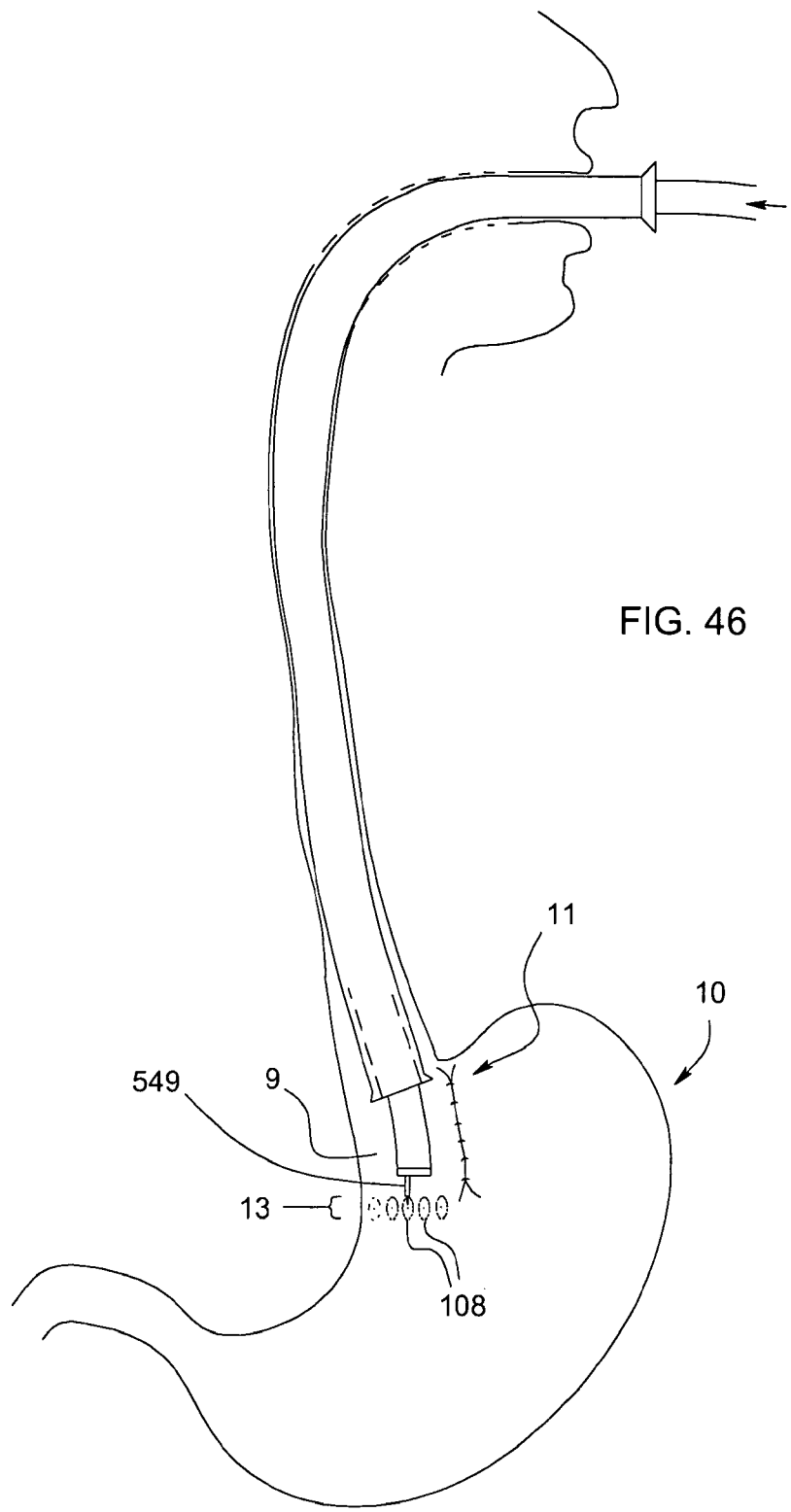
FIG. 46 is a cutaway view of a stomach which has undergone the gastric partition procedure shown in FIG. 22, showing an endoscopic device modifying the stomach walls near the outlet of the gastric pouch to create a restriction.

Yet another approach to creating a restrictive outlet 13 to a gastric pouch 9 is shown in FIG. 46, wherein an endoscopic injection needle 549 is shown injecting pockets of a bulking agent between the mucosa 28 and the muscularis 24. A number of appropriate bulking agents are known to those skilled in the art, including, but not limited to, those derived from natural tissue, for example human and animal collagen, muscle, fat and cartilage, and those derived from synthetic materials, such as silicone, polymethylmethacrylate, polyethylene, polypropylene, polypropylene, Delrin, and Teflon. Such materials may be bioreactive, in that their properties change once implanted, as in the case of expandable hydrogels, ethyl vinyl alcohol and water-swellable polymers. Such bulking agents may be injectable as in the case of a solution, suspension, slurry or paste, and may be combined with a carrier to assist with injection or to enhance biocompatibility. Alternatively, the bulking agent may be inserted in a pre-formed shape, as in the case of a sponge, expandable hydrogel prosthesis or bladder.

Figure 48:
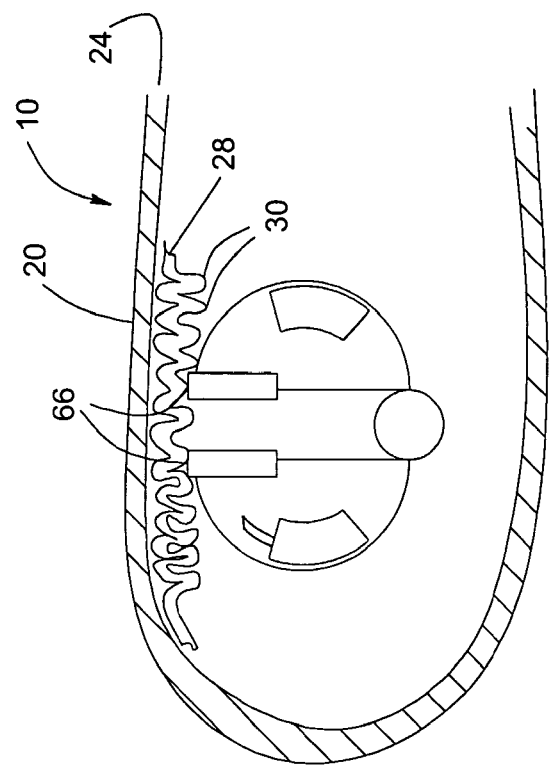
FIG. 48 is a section view showing the endoscopic device of FIG. 47 engaging the mucosa.
Figure 47:
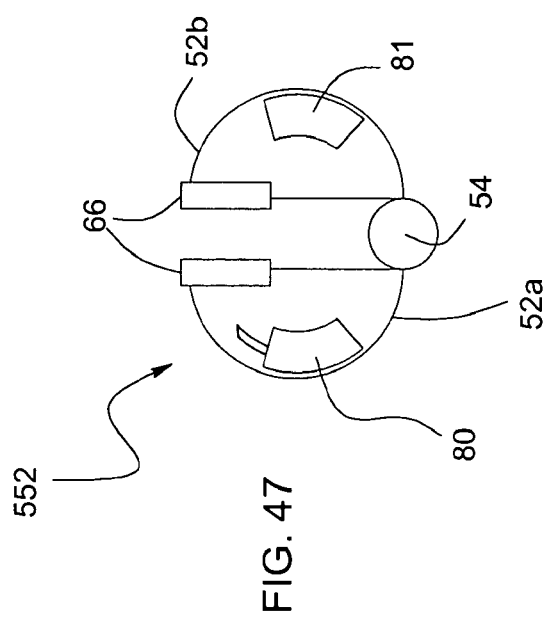
FIG. 47 is a section view showing an endoscopic device configured to invaginate and secure a fold of stomach wall.
Figure 52:
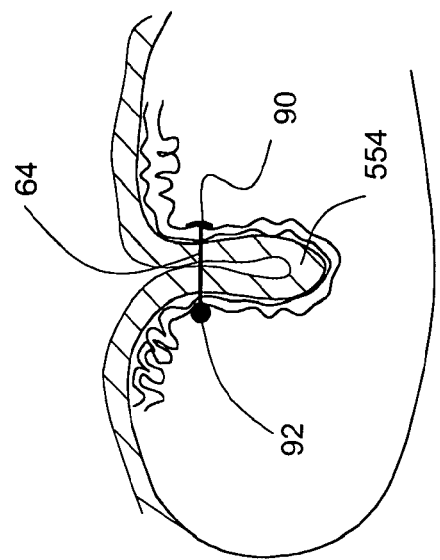
FIG. 52 is a section view of the stomach of FIG. 51 after deployment of the securement device and removal of the endoscopic device.
Figure 51:
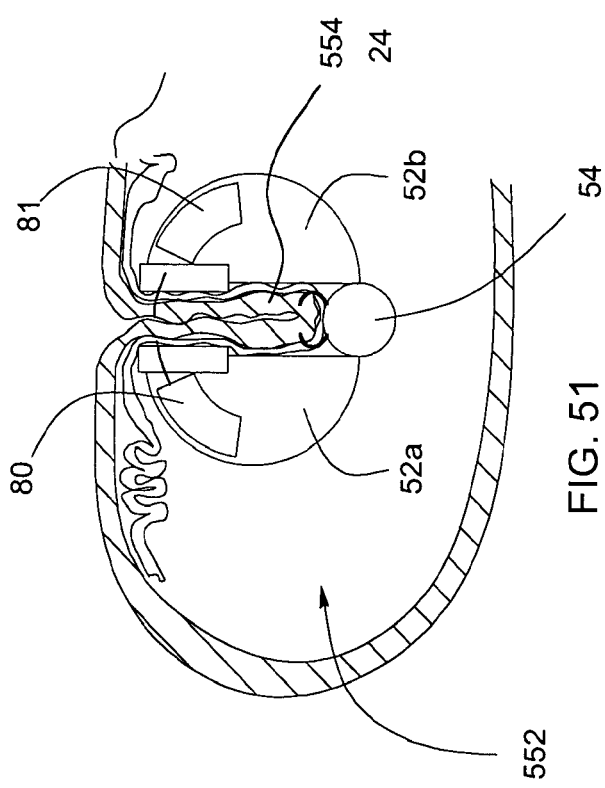
FIG. 51 is a section view showing the endoscopic device of FIG. 47 shown having invaginated a fold of the stomach wall and deploying a securement device.

Still another combination of a device and method for creating a gastric restriction is shown in FIGS. 47-53a. In FIG. 47, a side section view of a device 552 similar to device 50 described previously is shown, having analogous elements including hinge 54, case halves 52a and 52b, tissue engagement mechanisms 66, a tissue securement deployment carriage 80 and needle catcher 81. In FIG. 48, device 552 is shown in the lumen of stomach 10 with tissue engagement mechanisms 66 engaging the mucosa 28. In FIG. 49, hinge 54 is opened, causing the spreading of mucosa 28 and rugae 30. This spreading procedure may be carried out iteratively until the mucosa is adequately flattened. In FIG. 50, hinge 54 of device 552 is fully opened and hooks 151 are deployed to engage the muscularis 24. Once the muscularis 24 has been engaged, hinge 54 closes, bringing halves 52a and 52b together and pulling an invaginated fold of stomach into the cavity of device 552. Securement carriage 80 is then deployed, pushing a needle 62 (not shown) carrying a suture 64 (not shown) similar to that shown in FIG. 11a is pushed through the top of invaginated fold 554. FIG. 52 depicts the completed procedure showing suture 64 and anchor elements 90 and 92 securing the fold.

Figure 53:
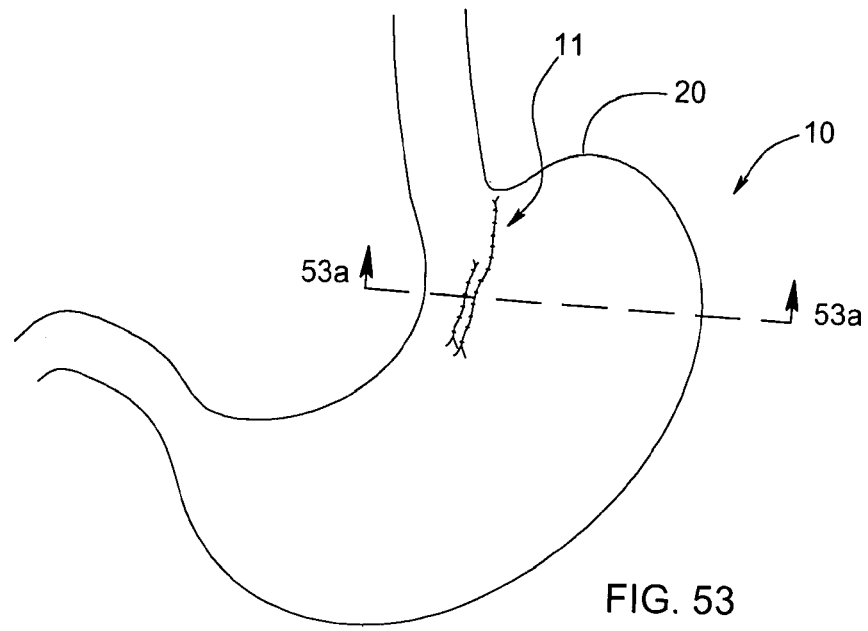
FIG. 53 is an anterior schematic view of a stomach that has undergone the invagination procedure shown in FIGS. 48-52 followed by a stitching procedure to create a gastric partition as well as to create a restrictive outlet by trapping the invaginated fold at the outlet of the pouch.
Figure 53A:
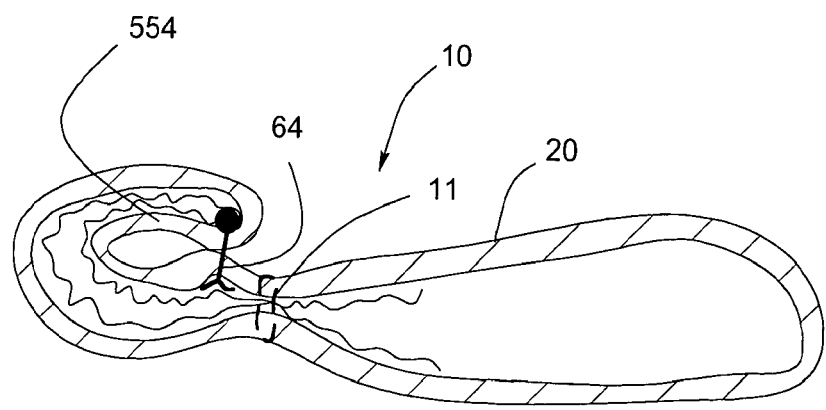
FIG. 53a is a section view taken along line 53a-53a in FIG. 53 showing the invaginated fold 554 trapped in the lumen of restrictive outlet 13.

When the procedure illustrated in FIGS. 47-52 is combined with a stitching procedure similar to that shown in FIG. 43, the outcome is shown in FIGS. 53 and 53a. As can be seen in FIG. 53, a gastric pouch and restrictive outlet are formed, similar to that in FIG. 43. However, as illustrated in FIG. 53a, the invaginated fold 554 is trapped in the lumen of restrictive outlet 13, creating a natural and highly effective restrictive to flow.

It will be appreciated that dilation of the restrictive outlet 13 over time is a concern and that the same techniques described herein for minimizing the dilation of the gastric pouch 9 can be applied to the restrictive outlet 13.

Although certain embodiments and examples have been described herein, it will be understood by those skilled in the art that many aspects of the methods and devices shown and described in the present disclosure may be combined differently and/or modified to form still further embodiments. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

What is claimed is:

1. An apparatus for creating a partition in a stomach cavity, comprising:
   a proximal user control portion, a distal trans-oral portion configured and shaped to be trans-orally insertable at least partially into a stomach cavity, and a plurality of control modules extending from the user control portion to the trans-oral portion;
   wherein the trans-oral portion includes:
      at least two tissue engagement assemblies, each assembly configured to engage a different target region of a stomach cavity wall;
      means for approximating the target regions engaged by the at least two tissue engagement assemblies; and
      at least one tissue securement assembly configured to securely and fixably couple tissue regions approximated by the means for approximating; and
   wherein a first control module of the plurality of control modules is operatively coupled to the at least two tissue engagement assemblies and is configured to cause each tissue engagement assembly to engage a different target tissue region upon user activation;
   a second control module of the plurality of control modules is operatively coupled to the means for approximating and causes the means for approximating to approximate target regions engaged by the tissue engagement assemblies upon user activation; and
   a third control module of the plurality of control modules is operatively coupled to the at least one tissue securement assembly and causes the at least one tissue securement assembly to securely and fixably couple tissue regions approximated by the means for approximating upon user activation.

2. The apparatus for creating a partition in a stomach cavity of claim 1, wherein the each of the plurality of control modules includes one of a push-wire, a pull-wire, a cable, a chain, a belt, and a spring.

3. The apparatus for creating a partition in a stomach cavity of claim 1, wherein the at least one tissue securement assembly deploys securements including one of sutures, staples and t-tags to securely and fixably couple tissue regions approximated by the means for approximating.

4. The apparatus for creating a partition in a stomach cavity of claim 3, wherein the securements are formed from a biocompatible material.

5. The apparatus for creating a partition in a stomach cavity of claim 1, wherein the at least one tissue securement assembly deploys a single one securement, the securement one of a suture, a staple, and a t-tag to securely and fixably couple tissue regions approximated by the means for approximating each time the third control module is activated by a user.

6. The apparatus for creating a partition in a stomach cavity of claim 1, wherein the at least one tissue securement assembly deploys a plurality of securements, the securements one of sutures, staples, and t-tags to securely and fixably couple tissue regions approximated by the means for approximating each time the third control module is activated by a user.

7. The apparatus for creating a partition in a stomach cavity of claim 6, wherein the proximal user control portion includes a suction port, the trans-oral portion includes a suction port, and the apparatus further includes a suction conduit between the proximal user control portion suction port and the trans-oral portion suction port enabling suction to be applied to the trans-oral portion to collapse stomach walls around the trans-oral portion when deployed in a stomach cavity.

8. The apparatus for creating a partition in a stomach cavity of claim 1, wherein each of the at least tissue engagement assemblies include one of a hook, a needle, and a barb.

9. The apparatus for creating a partition in a stomach cavity of claim 1, wherein a portion of each of the at least two tissue engagement assemblies is configured to engage a different target region and change its trans-oral position after target region engagement to stretch out rugal folds along the stomach wall at the engaged different target regions.

* * * * *